US010101341B2

(12) United States Patent
Bodo et al.

(10) Patent No.: US 10,101,341 B2
(45) Date of Patent: Oct. 16, 2018

(54) BIOMARKERS OF IMMUNOTHERAPY EFFICACY

(75) Inventors: Véronique Bodo, Palaiseau (FR); Philippe Moingeon, Verrieres le Buisson (FR); Julien Bouley, Montrouge (FR); Emmanuel Nony, Antony (FR); Hélène Moussu, Monthlery (FR); Karine Jain, Versailles (FR)

(73) Assignee: STALLERGENES, Antony (FR)

( * ) Notice: Subject to any disclaimer, the term of this patent is extended or adjusted under 35 U.S.C. 154(b) by 176 days.

(21) Appl. No.: 14/110,242

(22) PCT Filed: Apr. 6, 2012

(86) PCT No.: PCT/IB2012/051721
§ 371 (c)(1),
(2), (4) Date: Dec. 13, 2013

(87) PCT Pub. No.: WO2012/137180
PCT Pub. Date: Oct. 11, 2012

(65) Prior Publication Data
US 2014/0112955 A1    Apr. 24, 2014

(30) Foreign Application Priority Data
Apr. 6, 2011  (EP) .................................... 11305401

(51) Int. Cl.
*G01N 33/53*    (2006.01)
*G01N 33/68*    (2006.01)

(52) U.S. Cl.
CPC ..... *G01N 33/6893* (2013.01); *G01N 33/6863* (2013.01); *G01N 2333/523* (2013.01); *G01N 2333/71* (2013.01); *G01N 2333/775* (2013.01); *G01N 2333/8128* (2013.01); *G01N 2800/24* (2013.01); *G01N 2800/52* (2013.01); *G01N 2800/60* (2013.01)

(58) Field of Classification Search
None
See application file for complete search history.

(56) References Cited

FOREIGN PATENT DOCUMENTS

WO    WO 2007/106762    9/2007
WO    WO 2008/157518    12/2008

OTHER PUBLICATIONS

Stefan et al. 'Plasma Fetuin-A Levels and the Risk of Type 2 Diabetes.' Diabetes 57:2762-2767, 2008.*
Haenan et al. 'Proteome analysis of multiple compartments in a mouse model of chemical-induced asthma.' J. Prot. Research. 9:5868-5876, 2010.*
UniProtKB: locus FETUA_HUMAN, accession P02765.*
Caillot et al. 'Sialylated Fetuin-A as a candidate predictive biomarker for successful grass pollen allergen immunotherapy.' J. Allergy Clin Immunol. 2017 in press.*
Di Lorenzo, G. et al. "Evaluation of serum s-IgE/total IgE ration in predicting clinical response to allergen-specific immunotherapy" *Journal of Allergy and Clinical Immunology*, May 1, 2009, pp. 1103-1110. vol. 123, No. 5.
Fujimura, T. et al. "Increase of regulatory T Cells and the ratio of specific IgE to total IgE are candidates for response monitoring or prognostic biomarkers in 2-year sublingual immunotherapy (SLIT) for Japanese cedar pollinosis" *Clinical Immunology*, Apr. 1, 2011, pp. 65-74, vol. 139.
Zhao, L. et al. "Identification of Candidate Biomarkers of Therapeutic Response to Docetaxel by Proteomic Profiling" *Cancer Research*, Oct. 1, 2009, pp. 7696-7703, vol. 69, No. 19.
Signor, L. et al. "Two-dimensional electrophoresis protein profiling and identification in rat bronchoalveolar lavage fluid following allergen and endotoxin challenge" *Proteomics*, Jul. 1, 2004, pp. 2101-2110, vol. 4, No. 7.
Wang, H. et al. "A pathway-based approach to find novel markers of local glucocorticoid treatment in intermittent allergic rhinitis" *Allergy*, 2011, pp. 132-140, vol. 66, No. 1.
Mourey, L. et al. "Antithrombin III: structural and functional aspects" *Biochimie*, Aug. 1, 1990, pp. 599-608, vol. 72, No. 8.
Cevit, O. et al. "Specific Allergen Immunotherapy: Effect on Immunologic Markers and Clinical Parameters in Asthmatic Children" *Journal of Investigational Allergology & Clinical Immunology*, Jan. 1, 2007, pp. 286-291, vol. 17. No. 5.
Jahnz-Rozyk, K. et al. "Cc-chemokine eotaxin as a marker of efficacy of specific immunotherapy in patients with intermittent IgE-mediated allergic rhinoconjunctivitis" *Allergy*, Jul. 1, 2003, pp. 595-601, vol. 58, No. 7.
Baron-Bodo, V. et al. "In search of biological markers for allergy immunotherapy" *Scientific Matters*, Jan. 1, 2010, pp. 9-11.

* cited by examiner

*Primary Examiner* — Nora M Rooney
(74) *Attorney, Agent, or Firm* — Salwanchik, Lloyd & Eisenschenk

(57) ABSTRACT

The invention relates to proteins for use as markers for the efficacy of sublingual immunotherapy. In particular, the proteins may be used to predict the responsiveness of a patient to immunotherapy. The invention may find use in selecting patients as suitable candidates for immunotherapy.

16 Claims, 15 Drawing Sheets

Specification includes a Sequence Listing.

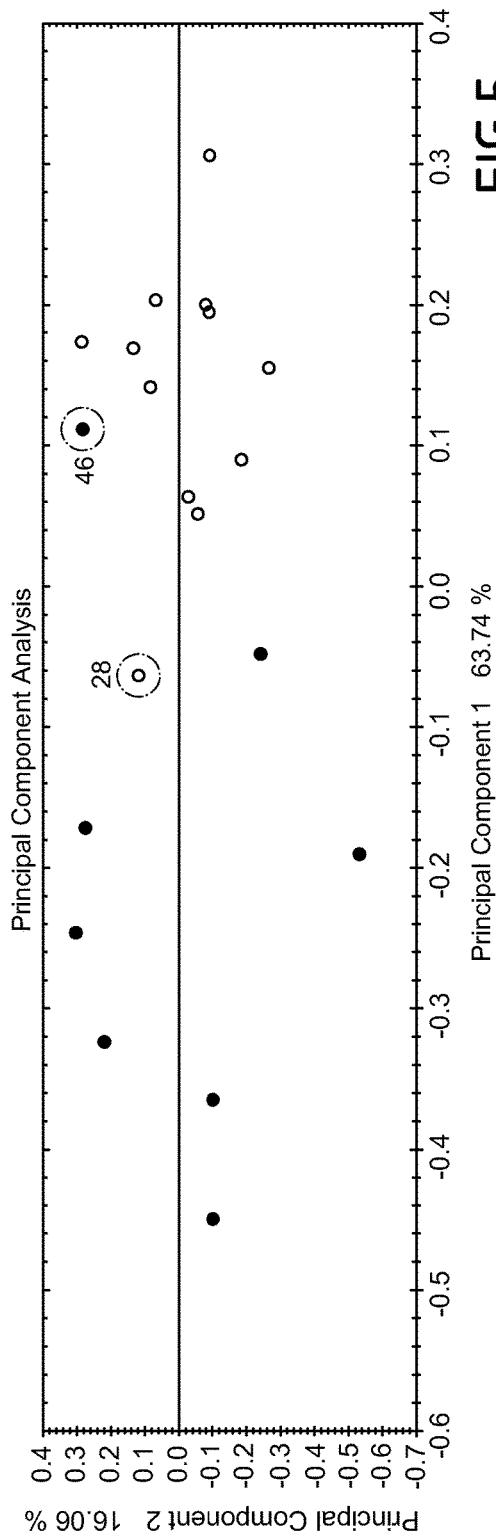
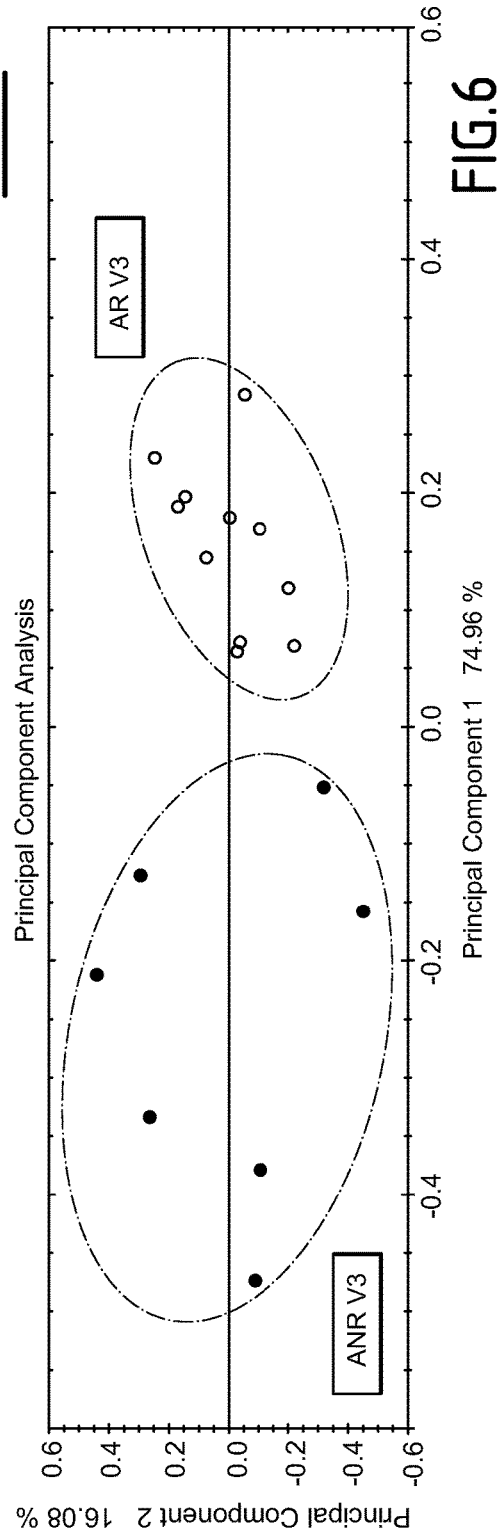
FIG.5
FIG.6

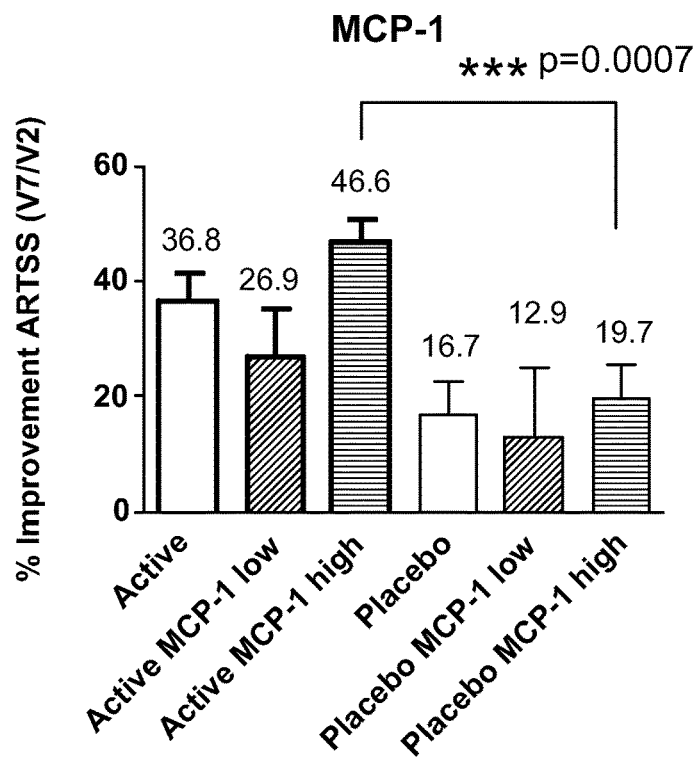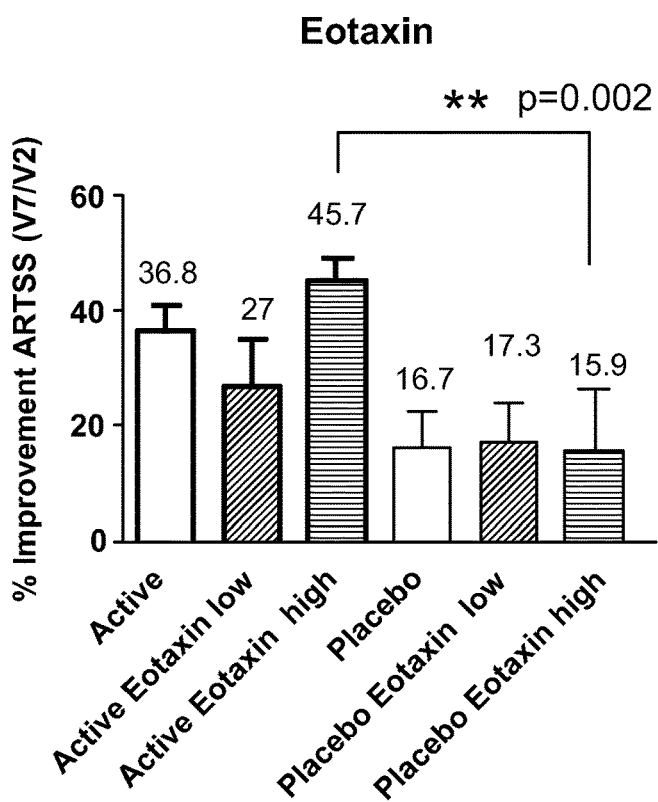
FIG. 9

MKSLVLLLCLAQLWGCHSAPHGPGLIYRQPNCDDPETEEAALVAIDYINQNLPWGYKHTL
NQIDEVKVWPQQPSGELFEIEIDTLETTCHVLDPTPVARCSVRQLKEHAVEGDCDFQLLK
LDGKFSVVYAKCDSSPDSAEDVRKVCQDCPLLAPLNDTRVVHAAKAALAAFNAQNNGSNF
QLEEISRAQLVPLPPSTYVEFTVSGTDCVAKEATEAAKCNLLAEKQYGFCKATLSEKLGG
AEVAVTCTVFQTQPVTSQPQPEGANEAVPTPVVDPDAPPSPPLGAPGLPPAGSPPDSHVL
LAAPPGHQLHRAHYDLRHTFMGVVSLGSPSGEVSHPRKTRTVVQPSVGAAAGPVVPPCPG
RIRHFKV

FIG.11

MISPVLILFSSFLCHVAIAGRTCPKPDDLPFSTVVPLKTFYEPGEEITYSCKPGYVSRGG
MRKFICPLTGLWPINTLKCTPRVCPFAGILENGAVRYTTFEYPNTISFSCNTGFYLNGAD
SAKCTEEGKWSPELPVCAPIICPPPSIPTFATLRVYKPSAGNNSLYRDTAVFECLPQHAM
FGNDTITCTTHGNWTKLPECREVKCPFPSRPDNGFVNYPAKPTLYYKDKATFGCHDGYSL
DGPEEIECTKLGNWSAMPSCKASCKVPVKKATVVYQGERVKIQEKFKNGMLHGDKVSFFC
KNKEKKCSYTEDAQCIDGTIEVPKCFKEHSSLAFWKTDASDVKPC

FIG.12

MYSNVIGTVTSGKRKVYLLSLLLIGFWDCVTCHGSPVDICTAKPRDIPMNPMCIYRSPEK
KATEDEGSEQKIPEATNRRVWELSKANSRFATTFYQHLADSKNDNDNIFLSPLSISTAFA
MTKLGACNDTLQQLMEVFKFDTISEKTSDQIHFFFAKLNCRLYRKANKSSKLVSANRLFG
DKSLTFNETYQDISELVYGAKLQPLDFKENAEQSRAAINKWVSNKTEGRITDVIPSEAIN
ELTVLVLVNTIYFKGLWKSKFSPENTRKELFYKADGESCSASMMYQEGKFRYRRVAEGTQ
VLELPFKGDDITMVLILPKPEKSLAKVEKELTPEVLQEWLDELEEMMLVVHMPRFRIEDG
FSLKEQLQDMGLVDLFSPEKSKLPGIVAEGRDDLYVSDAFHKAFLEVNEEGSEAAASTAV
VIAGRSLNPNRVTFKANRPFLVFIREVPLNTIIFMGRVANPCVK

FIG.13

MKVSAALLCLLIAATFIPQGLAQPDAINAPVTCCYNFTNRKISVQRLASYRRITSSKCP
KEAVIFKTIVAKEICADPKQKWVQDSMDHLDKQTQTPKT

FIG.14

MKVSAALLWLLLIAAAFSPQGLAGPASVPTTCCFNLANRKIPLQRLESYRRITSGKCPQK
AVIFKTKLAKDICADPKKKWVQDSMKYLDQKSPTPKP

FIG.15

BIOMARKERS OF IMMUNOTHERAPY EFFICACY

The Sequence Listing for this application is labeled "Seq-List-replace.txt" which was created on Jan. 11, 2017 and is 15 KB. The entire contents of the sequence listing are incorporated herein by reference in their entirety.

The invention concerns the identification of proteins which can be used as markers for the efficacy of immunotherapy, in particular sublingual immunotherapy for grass pollen allergy.

BACKGROUND

Allergy is a major and growing health concern around the world. As societies become more affluent and reduce the incidence of contagious disease, the prevalence of allergic disease increases. Finding effective treatments for allergy, both preventive and therapeutic, is a growing challenge for today's healthcare industry. Traditionally, management of allergy has concentrated on alleviation of symptoms, using antihistamines and medications which relieve allergic symptoms including nasal congestion, dermatitis and asthma, such as decongestants, creams, anti-inflammatories and bronchodilators. Allergen avoidance is another strategy for allergy management, but this is often difficult or impossible, particularly in the case of pervasive allergens such as pollen. A third alternative is specific allergy vaccination, in which patients are inoculated with the allergen causing the allergy in order to obtain an improvement in the patient's immune status. This kind of treatment has the advantage of altering the course of the illness to prevent the manifestation of symptoms, rather than simply alleviating symptoms.

Injective immunotherapy (subcutaneous immunotherapy or SCIT) was first reported in 1911 and has been used in clinical practice since the 1970s. However, the invasive nature of the therapy, requiring regular clinician visits, and problems with side effects—including, in rare cases, anaphylaxis and death—have prevented it from being a routinely used treatment of allergy. Immunotherapy via administration of allergen to mucosa, such as the oral mucosa of the mouth and gut, has also been explored. Sublingual immunotherapy (SLIT), in which the vaccine is administered underneath the tongue and absorbed via the sublingual mucosa, is a well-established alternative to injective immunotherapy. SLIT has been shown to be comparable to SCIT in terms of efficacy and has a superior safety profile. It is now generally preferred to SCIT due to the less invasive nature to the technique and the lower risk of side effects, as the occurrence of harmful side effects from SLIT is relatively low. However, the expense of the treatment is still a major factor in slowing down the uptake of SLIT. Identifying methods of pre-selecting patients likely to respond well to the therapy is thus of interest, as is the identification of methods of tracking patient response to therapy.

SUMMARY OF THE INVENTION

The inventors have identified proteins which are expressed at a higher level in patients who responded well to SLIT for grass pollen allergy than in patients who responded less well. These proteins thus have potential as markers for efficacy of immunotherapy, in particular as predictive markers of use in selecting patients who will respond to immunotherapy. The increased level of these proteins in patients who respond to immunotherapy indicates that the proteins themselves may play a role in the desensitization process, and thus that the proteins also have potential therapeutic efficacy.

In its broadest aspect, the invention relates to the use of any one or more of the marker proteins disclosed herein as a marker for the efficacy of immunotherapy. In a preferred embodiment, the marker protein is used to predict the responsiveness of a patient to immunotherapy. In another embodiment, the marker protein is used to determine the efficacy of immunotherapeutic treatment. The invention may find use in selecting patients as suitable candidates for immunotherapy.

Thus, the invention provides a method of predicting responsiveness of a patient to immunotherapy, which method comprises detecting the level of expression of at least one marker protein as disclosed herein in a biological sample from said patient. Further provided is a method of determining the efficacy of immunotherapy, which method comprises detecting the level of expression of at least one marker protein as disclosed herein in a biological sample from said patient.

The invention further provides a method of predicting responsiveness of a patient to immunotherapy, which method comprises the steps:

a) detecting the level of expression of at least one marker protein as disclosed herein in a biological sample from said patient, (b) comparing the level of expression of said protein with a control sample or a control standard, and c) identifying said patient as likely to respond to immunotherapy based on said comparison.

Further provided is a method of selecting a patient for immunotherapy, the method comprising (a) detecting the level of expression of at least one marker protein as disclosed herein in a biological sample from said patient, (b) comparing the level of expression of said protein or combination of proteins with a control sample or a control standard, and (c) selecting the patient for therapy based on said comparison.

Also disclosed herein is a method of predicting responsiveness of a patient to immunotherapy, the method comprising:

(i) obtaining a serum sample from said patient;
(ii) optionally depleting the crude human serum up to three times using Agilent MARS Human-14 spin cartridge according to manufacturer's protocol;
(iii) pooling the samples into a spin concentrator (5 kDa molecular mass cut-off) and spinning at 5000 g for 35 minutes at 10° C.;
(iv) precipitating the protein with a commercial 2D clean-up kit according to GE Healthcare's protocol;
(v) solubilising in a 2D sample solution containing 7M urea, 2M thiourea, 4% Chaps and 30 mM Tris pH 8.8;
(vi) labelling samples with CyDye (CyDye DiGE Fluor kit, GE Healthcare), using a ratio of 400 pmoles/50 µg proteins;
(vii) separating proteins on 24 cm long Immobiline pH 4-7 DryStrip gels by IEF using the IPGphor system 3, using the following protocol:
  a. focusing of proteins by increasing the applied voltage up to 10,000 V for a total of 72750 V·h using the following steps: Phase 1: 50 V-300 V (1 h30); Phase 2: 300 V-3000 V (2 h); Phase 3: 3000 V (2 h30); Phase 4: 3000 V-10,000 V (2 h); Phase 5: 10,000 V (5 h);
  b. equilibration of strips in urea-containing buffer (reduction and alkylation); and c. loading onto SDS polyacrylamide gels (11%) for separation according to molecular mass using an Ettan DALT Six Electrophoresis System (GE Healthcare);

(viii) identifying a marker protein as disclosed herein by analyzing said gels with SameSpots software (NonLinear Dynamics); and (ix) comparing the expression of said marker protein to that of a control as disclosed herein.

Also provided is a marker protein as disclosed herein for use in a method as disclosed herein of predicting responsiveness to immunotherapy, in particular sublingual immunotherapy of grass pollen allergy.

Also provided is a marker protein as disclosed herein for use in therapy, in particular immunotherapy such as allergen immunotherapy or autoantigen immunotherapy, for example for the treatment of an autoimmune disorder. Said protein may for example be administered to a patient with an autoimmune disorder or a patient undergoing allergen immunotherapy. It may be administered with the allergen in the course of the immunotherapeutic regime, or administered as an additional agent to a patient undergoing or who has undergone allergen immunotherapy.

Further provided is a kit for use in determining responsiveness of a patient to immunotherapy, which kit comprises a detection agent as described herein for detecting a marker protein as disclosed herein, and optionally instructions for using said agent to predict responsiveness of said patient to therapy.

Marker Proteins

The marker protein is selected from the group consisting of Fetuin-A (also known as alpha-2-HS-glycoprotein), beta-2 glycoprotein 1, Antithrombin-III, MCP1, Eotaxin and any other protein identified in the Examples herein as differentially expressed in responder subjects compared to non-responder subjects.

The term 'marker protein' includes all isoforms of said proteins. Thus, for the marker proteins described above, the term 'marker protein' includes the polypeptide having the amino acid sequences disclosed herein and all isoforms thereof. 'Isoform' refers to all alternative forms of a protein, for example alternatively spliced versions and post-translationally modified forms such as glycoforms. Post-translationally modified isoforms may include acetylated, formylated, lipoylated, myristoylated, palmitoylated, alkylated, methylated, amidated, glycosylated, hydroxylated, nitrosylated, phosphorylated, sulphated, polysialylated and sialylated forms. Isoforms include naturally occurring variants, allelic variants, SNPs (single nucleotide polymorphisms), alternative splice variants and truncated or secreted forms of the protein.

For instance, in the case of Fetuin-A, a difference in the amount of glycosylation may induce a shift of the Fetuin-A isoelectric point. Packer et al. (Biotechnology, 1996; 14:66-70) have detected a general increase of lactosamine (Gal-GlcNAc) repeats on the N-linked sugar antennary structures, which may affect the separation in the first dimension (i.e., an increase in protein pI). They also reported that the proportion of sialic acid relative to the neutral sugars did not appear to account for the separation of the isoforms. Phosphorylation, for example phosphorylation at position Ser 330, may also occur and may likewise induce a shift of the Fetuin-A isoelectric point.

Detection of the "level of expression" of a marker protein may refer to the level of expression of any individual isoform of said protein; the collective level of expression of selected isoforms of said protein; or the total level of expression of said protein including the reference sequence and all isoforms. For example, detection of the level of expression of Fetuin-A may include detection of the level of expression of a particular glycoform, a subset of glycoforms, all glycoforms, or all forms of Fetuin-A, whether modified or unmodified.

Known Fetuin-A isoforms are disclosed at Worldwide Website: uniprot.org/uniprot/P02765. They include post-translational modifications such as isoforms including phosphoserine at residue 134, 138, 325, 328, 330 and/or 334; N-linked GlcNAc at residue 156 and/or 176; O-linked GlcNAc at position 256, 270 and/or 346; disulphide bonds between positions 32 and 358, 89 and 100, 114 and 132, 146 and 149, 208 and 219, or 230 and 247; natural variants such as the substitution mutants V142L, T248M, T256S, D276N, and R317C; and pre- and processed forms comprising or lacking one or more of: the signal peptide (residues 1-18), the A chain (residues 19-300), the B chain (residues 341-367) and the connecting peptide (residues 301-340).

In one embodiment, the marker protein is (i) Fetuin-A having SWISS-PROT accession no. FETUA_HUMAN and/or the amino acid sequence shown in FIG. 11 (SEQ ID No 1); (ii) beta-2 glycoprotein having SWISS-PROT accession no. APOH_HUMAN and/or the amino acid sequence shown in FIG. 12 (SEQ ID No: 2); (iii) Antithrombin-III having SWISS-PROT accession no. ANT3_HUMAN and/or the amino acid sequence shown in FIG. 13 (SEQ ID No: 3); (iv) MCP-1 having SWISS-PROT accession no. CCL2_HUMAN and/or the amino acid sequence shown in FIG. 14 (SEQ ID No: 4); (v) Eotaxin having SWISS-PROT accession no. CCL11_HUMAN and/or the amino acid sequence shown in FIG. 15 (SEQ ID No: 5); (vi) the Fetuin-A isoform appearing at position 6, 7, 8 or 9 of FIG. 4; (vii) a Fetuin-A isoform shown in FIG. 16, in particular a Fetuin-A isoform appearing at position 428, 439 or 448 of FIG. 16; (viii) the beta-2 glycoprotein 1 isoform appearing at position 1 or 2 of FIG. 4; or (ix) the Antithrombin-III isoform appearing at position 3, 4 or 5 of FIG. 4. Said Fetuin-A isoform preferably has an isoelectric point of 4.5 to 4.7 and a molecular weight of 52 to 55 kDa. Said Fetuin-A isoform may be a phosphorylated isoform, for example an isoform which is phosphorylated on Ser 330 of SEQ ID No: 1.

Said proteins include those obtainable by the following method:

(i) obtaining a serum sample from said patient;
(ii) optionally depleting the crude human serum up to three times using Agilent MARS Human-14 spin cartridge according to manufacturer's protocol;
(iii) pooling the samples into a spin concentrator (5 kDa molecular mass cut-off) and spinning at 5000 g for 35 minutes at 10° C.;
(iv) precipitating the protein with a commercial 2D clean-up kit according to GE Healthcare's protocol;
(v) solubilising in a 2D sample solution containing 7M urea, 2M thiourea, 4% Chaps and 30 mM Tris pH 8.8;
(vi) labelling samples with CyDye (CyDye DiGE Fluor kit, GE Healthcare), using a ratio of 400 pmoles/50 µg proteins;
(vii) separating proteins on 24 cm long Immobiline pH 4-7 DryStrip gels by IEF using the IPGphor system 3, using the following protocol:
   a. isoelectric focusing by increasing the applied voltage up to 10,000 V for a total of 72,750 V·h using the following steps: Phase 1: 50 V-300 V (1 h30); Phase 2: 300 V-3000 V (2 h); Phase 3: 3000 V (2 h30); Phase 4: 3000 V-10,000 V (2 h); Phase 5: 10,000 V (5 h);
  b. equilibration of strips in urea-containing buffer (reduction and alkylation); and
  c. loading onto SDS polyacrylamide gels (11%) for separation according to molecular mass using an Ettan DALT Six Electrophoresis System (GE Healthcare); and
(viii) optionally, visualisation of spots and excision of protein-containing spots from the gel.

The biological sample may be, without limitation, blood, plasma, serum, nasal secretion, saliva, bronchoalveolar fluid or urine. The sample is preferably taken before the commencement of therapy or before the planned commencement of therapy. The sample may also be taken after the commencement of therapy, for example after one round of therapy is completed, in order to decide whether to proceed to further rounds. Where the method is a method of determining efficacy of therapy, the sample is preferably taken after the commencement of therapy.

In some embodiments, the methods of the invention involve detection of a single marker protein or protein isoform. In other embodiments, more than one protein or protein isoform is detected, for example at least 2, 3, 4, 5, 6, 7, 8, 9, 10, 11, 12, 13, 14 or 15 proteins or protein isoforms. In certain embodiments, a set of biomarkers comprising Fetuin-A and/or one or more isoforms thereof and at least 1, 2, 3, 4, 5 or 6 of the other biomarkers disclosed herein is detected. In other embodiments, a set of biomarkers comprising beta-2 glycoprotein 1 and/or one or more isoforms thereof and at least 1, 2, 3, 4, 5, 6, 7, 8, 9, 10, 11, 12 or 13 of the other biomarkers disclosed herein is detected. In other embodiments, a set of biomarkers comprising Antithrombin-III and/or one or more isoforms thereof and at least 1, 2, 3, 4, 5, 6, 7, 8, 9, 10, 11 or 12 of the other biomarkers disclosed herein is detected. In other embodiments, a set of biomarkers comprising MCP-1 and/or one or more isoforms thereof and at least 1, 2, 3, 4, 5, 6, 7, 8, 9, 10, 11 or 12 of the other biomarkers disclosed herein is detected. In other embodiments, a set of biomarkers comprising Eotaxin and/or one or more isoforms thereof and at least 1, 2, 3, 4, 5, 6, 7, 8, 9, 10, 11 or 12 of the other biomarkers disclosed herein is detected.

In some embodiments, the methods of the invention involve detection of phosphorylation on a peptide corresponding to a marker protein as described herein. For example, the method may involve detection of phosphorylation of a peptide comprising or consisting of the amino acid sequence of His318 to Arg337 of SEQ ID NO: 1. Phosphorylation of said peptide will preferably be phosphorylation at the position corresponding to Ser 330 of SEQ ID NO: 1. The phosphorylated peptide may be detected by mass spectrometry as described below.

An increase or decrease in the level of expression of a protein isoform may be detected in a patient sample compared to a control, as detailed below. The fold change in the patient sample compared to the control may be at least 1.2, at least 1.4, at least 1.6, at least 1.8, at least 2, at least 2.2, at least 2.4, at least 2.6, at least 2.8, at least 3, at least 3.5, at least 4, at least 4.5, at least 5, at least 6, at least 7 or at least 8-fold.

Control

The expression of the marker protein in the patient sample may be compared with a control standard value and/or or with the expression of said marker in a control sample. The control sample may be that of a control subject or subjects. The control subject may be, for example, a subject previously identified as a non-responder or poor responder to therapy, or a group of such subjects. Alternatively, the control subject may be a subject previously identified as a responder to therapy, or a group of such subjects. The control sample may also be obtained from a group of subjects selected at random. The control may also comprise an internal control. For example, a subset of a group of candidates for therapy may be selected for therapy by comparing the level of expression of a marker protein in all candidates and selecting those candidates with the highest level of expression for therapy. A standard value may be obtained by, for example, detecting the level of expression in a group of subjects and obtaining an average or median figure. The same controls may be selected where the method comprises detection of a characteristic other than, or additional to, level of expression. For example, post-translational modifications such as glycosylation may be detected, and where protein glycosylation state is determined, the glycosylation state in the patient sample may be compared with a standard and/or a control sample as described above.

As will be clear to the skilled person, the nature of the comparison of the patient sample with the control and the conclusions drawn will depend on the nature of the control. Where the marker protein is disclosed herein as a protein upregulated in responder subjects and the control is based on a non-responder subject or group of such subjects, a value the same as or similar to, or lower than, the control may be indicative of non-responsiveness to therapy, whereas a value higher than the control may be indicative of responsiveness to therapy. Conversely, where the control is based on a responder subject or group of such subjects, a value the same as or similar to, or higher than, the control may be indicative of responsiveness to therapy, whereas a value lower than the control may be indicative of non-responsiveness to therapy. Where the control is based on an average or median value obtained from a random group of subjects, a value higher than the control may be indicative of responsiveness to therapy.

Similarly, where the marker protein is disclosed herein as a protein downregulated in responder subjects and the control is based on a non-responder subject or group of such subjects, a value the same as or similar to, or higher than, the control may be indicative of non-responsiveness to therapy, whereas a value lower than the control may be indicative of responsiveness to therapy. Where the control is based on a responder subject or group of such subjects, a value the same as or similar to, or lower than, the control may be indicative of responsiveness to therapy, whereas a value higher than the control may be indicative of non-responsiveness to therapy. Where the control is based on an average or median value obtained from a random group of subjects, a value lower than the control may be indicative of responsiveness to therapy.

In some embodiments, the response to therapy may be predicted based on the relative expression or change in expression of different proteins or of different protein isoforms. For example, when compared with a control, the total collective level of expression of the isoforms of a particular protein in a sample may remain constant but the relative abundance of the different isoforms may change. The change of relative abundance of different isoforms compared to a control may also be of predictive value. It is thus possible for the same protein to be predictive of both responder and non-responder status, depending on the context.

In one embodiment, the control sample or standard is an average or mean value derived from a random sample of subjects, and the patient is identified as likely to respond to therapy or selected for therapy where the expression of the marker protein is higher in the patient sample than in the control sample or control standard. In another embodiment, the control is derived from a subject or group of subjects identified as responding to therapy, and the patient is identified as likely to respond to therapy or selected for therapy where the expression of the marker protein in the patient sample is the same as or higher than that in the control sample or control standard. Alternative controls are described herein and their use will be evident to the skilled person.

As explained above, 'level of expression' of a marker protein may refer to the level of expression of individual isoforms of said protein, collectively or individually, or it may refer to the total level of expression of said protein, which may include a combination of several isoforms, some of which may be overexpressed and others underexpressed in responders or non-responders. Thus, in one embodiment, altered expression of total levels of the marker protein compared to a control is indicative of a patient likely to respond to immunotherapy. In an alternative embodiment, a change in the absolute or relative amount of a protein isoform is indicative of a patient likely to respond to immunotherapy. In other embodiments, such changes may be indicative that a patient is not likely to respond to immunotherapy.

Detection of Proteins

The level of expression of the marker protein may be determined by gel electrophoresis (SDS-PAGE), in particular two-dimensional gel electrophoresis (2D-PAGE), carried out on the sample or a protein-containing extract thereof. 2D-PAGE is a well-established technique in which proteins are first separated in one dimension by isoelectric focusing and further separated by SDS-PAGE along a second dimension. Protein expression may be analysed by visualization of labeled proteins, or by Western blotting and immune detection. Protein quantification by 2D-PAGE is usually carried out by 2D-DiGE, in which proteins from a control sample and the test sample are labeled with different dyes. The dyes are mass- and charge-matched so the labeled proteins migrate to the same position on the gel, allowing quantification to be carried out within a single gel.

Protein expression may also be determined by mass analysis, such as mass spectrometry. Qualitative and quantitative mass spectrometric techniques are known and used in the art. A quantitative LC-MS/MS can also be used.

Expression may also be determined using an antibody which binds to the protein, for example a monoclonal or polyclonal antibody, an antibody variant or fragment such as a single chain antibody, a diabody, a minibody, a single chain Fv fragment (sc(Fv)), a Sc(Fv)$_2$ antibody, a Fab fragment or a F(ab')$_2$ fragment, a V$_H$H antibody or a single domain antibody. The antibody may be mono-, bi-, tri- or multivalent. The antibody may be immobilized on a solid support. Antibodies may be used to determine protein expression in a range of immunological assays including competitive and non-competitive assay systems using techniques such as Western blotting, radioimmunoassays such as RIA (radio-linked immunoassay), ELISA (enzyme-linked immunosorbent assay), "sandwich" immunoassays, immunoprecipitation assays, immunodiffusion assays, agglutination assays, complement-fixation assays, immunoradiometric assays, fluorescent immunoassays, e.g., FIA (fluorescence-linked immunoassay), chemiluminescence immunoassays, electrochemiluminescence immunoassays (ECLIA) and protein A immunoassays. Such assays are routine and well known to the person skilled in the art.

Expression may alternatively be determined using a protein-specific aptamer. An aptamer is a short peptide capable of specifically binding to a specific protein sequence, consisting of a variable peptide loop attached at both ends to a protein scaffold. Methods for making protein aptamers are well known in the art, the most commonly used method being the yeast two-hybrid system. Such aptamers may preferably be labeled in order to allow the detection of a protein-ligand interaction. A nanotechnology-based assay could also be used.

Therapeutic Applications

'Allergy' is a condition characterized by production of allergen-specific IgE in response to a specific allergen, usually a protein. Clinical manifestations and symptoms of allergy may include nasal congestion, nasal pruritis, ocular pruritis, tearing, rhinorrhea, sinusitis, rhinitis, sneezing, wheezing, conjunctivitis, dermal itching, dermatitis, skin irritation and asthma.

An 'allergen' is a substance, usually a protein, which elicits the production of IgE antibodies in predisposed individuals. Allergens may include pollen allergens (such as tree, herb, weed and grass pollen allergens), insect allergens (such as inhalant, saliva and venom allergens, e.g., cockroach, midge and house dust mite allergens and hymenoptera venom allergens), animal hair and dander allergens (from, e.g., dog, cat, horse, rat, mouse, or rabbit) and food allergens. In a preferred embodiment, the patient has grass pollen allergy and the immunotherapy uses grass pollen allergen.

For instance, a protein allergen may be selected from the group consisting of a protein allergen of the genus *Dermatophagoides*; a protein allergen of the genus *Felis*; a protein allergen of the genus *Ambrosia*; a protein allergen of the genus *Lolium*; a protein allergen of the genus *Cryptomeria*; a protein allergen of the genus *Alternaria*; a protein allergen of the genus Alder; a protein allergen of the genus *Betula*; a protein allergen of the genus of *Blomia*; a protein allergen of the genus *Quercus*; a protein allergen of the genus *Olea*; a protein allergen of the genus *Artemisia*; a protein allergen of the genus *Plantago*; a protein allergen of the genus *Parietaria*; a protein allergen of the genus Canine; a protein allergen of the genus *Blattella*; a protein allergen of the genus *Apis*; a protein allergen of the genus *Cupressus*; a protein allergen of the genus Thuya; a protein allergen of the genus *Chamaecyparis*; a protein allergen of the genus *Periplaneta*; a protein allergen of the genus *Agropyron*; a protein allergen of the genus *Secale*; a protein allergen of the genus *Triticum*; a protein allergen of the genus *Cynorhodon*; a protein allergen of the genus *Juniperus*; a protein allergen of the genus *Dactylis*; a protein allergen of the genus *Festuca*; a protein allergen of the genus *Poa*; a protein allergen of the genus *Avena*; a protein allergen of the genus *Holcus*; a protein allergen of the genus *Anthoxanthum*; a protein allergen of the genus *Arrhenatherum*; a protein allergen of the genus *Agrostis*; a protein allergen of the genus *Phleum*; a protein allergen of the genus *Phalaris*; a protein allergen of the genus *Paspalum*; and a protein allergen of the genus *Sorghum*.

Examples of various known protein allergens derived from some of the above-identified genera include: *Betula* (*verrucosa*) Bet v I; Bet v II; *Blomia* Blo 11; Blot III; Blo t V; Blo t XII; *Cynorhodon* Cyn d I; *Dermatophagoides* (*pteronyssinus* or *farinae*) Der p I; Der p II; Der p III; Der p VII; Der f I; Der f II; Der f III; Der f VII; *Felis* (*domesticus*) Fel d I; *Ambrosia* (artemiisfolia) Amb a 1.1; Amb a 1.2; Amb a 1.3; Amb a 1.4; Amb a II; *Lolium* (*perenne*) Lol p I; Lot p II; Lol p III; Lot p IV; Lol p IX (Lol p V or Lol p Ib); *Cryptomeria (japonica)* Cry j I; Cry j II; *Canis (familiaris)* Can f I; Can f II; *Juniperus (sabinoides or virginiana)* Jun s I; Jun v I; *Juniperus (ashei)* Jun a I; Jun a II; *Dactylis (glomerata)* Dae g I; Dae g V; *Poa (pratensis)* Poa p I; Phl p I; Phl p V; Phl p VI; and *Sorghum (halepensis)* Sor h I.

In autoimmune disorders, the immune system produces antibodies to an endogenous antigen. Antibody-coated cells, like any similarly coated foreign particle, activate the complement system, resulting in tissue injury. Most human autoimmune disorders are specific antigen-driven T-cell diseases. T-cell clones responding to specific antigenic epitopes are responsible for the initiation and/or the propagation of these diseases. Similarly, specific antigen-driven T-cell responses are responsible for the rejection of organ allografts and the immune response to tumors. Activated T-cells provide the "engine" for the chronic inflammation that is associated with autoimmune disorders. Autoimmune disorders include but are not limited to rheumatoid arthritis (RA), multiple sclerosis (MS), inflammatory bowel disease (IBD), systemic lupus erythematodes (SLE), Graves' disease and diabetes mellitus. "Immunotherapy" refers to the administration of an allergen or autoantigen to a patient with the aim of reducing current or future immune response, such as an IgE response, and/or manifestation of clinical symptoms of an allergy or an autoimmune disorder. Immunotherapy is conventionally carried out by repeatedly administering a monodose or incremental doses of an allergen to a patient in need thereof, thereby resulting in an adaptive immune response of the patient who becomes desensitized to the allergen.

Immunotherapy may comprise administration of an allergen to a mucosal surface, optionally a sublingual, oral, buccal, ocular, rectal, urinal, pulmonary or otolar surface. In particular, immunotherapy may be sublingual immunotherapy. Alternatively, immunotherapy may comprise administration via a parenteral route, such as subcutaneously or intravenously, for example via injection, or via alternative routes such as intranasal, skin immunisation, e.g., transdermal, or intralymphatic administration.

The allergen used for immunotherapy may be a single allergenic substance or a mixture of such substances, for example a mixture of proteins. It may be a partially or fully purified extract, such as a pollen extract, a recombinant protein, a hypoallergen or a peptide derived therefrom. For example, where the immunotherapy is used to treat grass pollen allergy, the allergen administered for immunotherapy may be a grass pollen extract from the pollen of one or several genera of grasses, such as *Dactylis, Poa, Lolium, Anthoxanthum* and *Phleum*. The allergen may also be an allergoid, i.e., a chemically modified form of a naturally occurring allergen which has been chemically modified (for example by aldehydation). The allergen may be administered in conjunction with an adjuvant.

Immunotherapy may further comprise administration of an additional agent, for example a marker protein as defined herein. Said additional agent is preferably administered to a patient undergoing allergen immunotherapy. For example, it may be administered with the allergen in the course of the immunotherapeutic regime, or administered as an additional agent to a patient undergoing or who has undergone allergen immunotherapy. Said additional agent may be formulated with the allergen and administered in combination with the allergen, administered simultaneously with the allergen but in separate form, or administered separately as an adjunct to allergen administration.

'Response' of a patient to treatment indicates that the patient manifests a reduction in the clinical symptoms of allergy. Clinical symptoms may be assessed over the course of treatment, i.e., symptoms before treatment may be compared to symptoms during and after treatment. Alternatively, a reduction in symptoms may be determined by comparison to a baseline level established before treatment. This approach is particularly useful where, for example, immunotherapy is carried out in patients not currently experiencing symptoms, as may be the case for seasonal grass pollen allergy sufferers, who may be treated before the pollen season. Symptoms may be assessed by standard methods, such patient self-assessment or recordation of the amount of medication required. The degree of a patient's response to treatment may be assessed by measuring the degree of reduction in severity of symptoms, for example as described in the experimental section below. A 'responder' subject as defined herein is a subject who responds to immunotherapy with an improvement in clinical symptoms, preferably a statistically significant improvement, as compared to patients receiving placebo or no treatment. Preferably, a responder subject will demonstrate an improvement in clinical symptoms which is greater than the average or median improvement seen in a random sample of subjects. A 'nonresponder' subject is a subject who does not manifest any improvement in clinical symptoms following immunotherapy, or who demonstrates a non-statistically significant improvement in symptoms, or who demonstrates an improvement in clinical symptoms which is less than the average or median improvement seen in a random sample of subjects. For example, where the allergy is grass pollen allergy, improvement in clinical symptoms may be detected by a reduction in the frequency or severity of nasal congestion, nasal pruritis, ocular pruritis, tearing, rhinorrhea, sinusitis, rhinitis, sneezing, wheezing and/or conjunctivitis.

'Therapy', 'therapeutic', 'treatment' or 'treating' include reducing, alleviating, inhibiting or eliminating the symptoms of allergy, as well as treatment intended to reduce, alleviate, inhibit or eliminate said symptoms. These terms may include preventive treatment which is intended to, or has the effect of, reducing, alleviating, inhibiting or eliminating future symptoms. They may also include treatment of ongoing symptoms.

'Patient' includes any individual who is a candidate for immunotherapy, including individuals not currently undergoing therapy. In most cases, the patient will be an individual who has, or has had at any time in the past, clinical symptoms of allergy and/or sensitization to an allergen and/or an allergen-specific IgE response, or an individual at risk of developing such symptoms. Sensitization to an allergen may be assessed by detecting IgE directed against allergen(s) from this source in the serum of the patient or by skin testing with a preparation containing the corresponding allergen(s). The allergen may without limitation include any of the allergens disclosed herein, in particular a grass pollen allergen. The patient is preferably a mammal, such as a rodent, a feline, a canine or a primate, and is preferably a human, in particular a child, a woman, or a man.

The invention will be further illustrated by reference to the following figures and examples. All documents referred to herein are hereby incorporated by reference in their entirety.

BRIEF DESCRIPTION OF THE FIGURES

FIG. 5: Principal component analysis (PCA) of Active Responder (AR) patients vs. Active Non Responder (ANR) patients at V3 before outlier exclusion.

FIG. 6: Principal component analysis (PCA) of Active Responder (AR) patients vs. Active Non Responder (ANR) patients at V3 after outlier exclusion.

FIG. 9: Clinical improvement in subgroups of patients defined on the basis of their low or high plasmatic expression of candidate biomarkers before treatment. Results shown for MCP-1 (left) and Eotaxin (right).

FIG. 11: Amino acid sequence of human Fetuin-A (SEQ ID NO: 1).

FIG. 12: Amino acid sequence of human beta-2 glycoprotein 1 (SEQ ID NO: 2).

FIG. 13: Amino acid sequence of human Antithrombin-III (SEQ ID NO: 3).

FIG. 14: Amino acid sequence of human MCP1 (SEQ ID NO: 4).

FIG. 15: Amino acid sequence of human Eotaxin (SEQ ID NO: 5).

EXAMPLES

Example 1: Study Design

A pharmacodynamic study was conducted to identify biomarkers predictive of SLIT efficacy.

The clinical protocol of the study was described in Horak, F. et al. (J. Allergy Clin. Immunol., 2009; 124:471-477). The study assessed the efficacy and onset of action of 5-grass-pollen tablets under controlled conditions provided by an allergen challenge chamber (ACC; also known as an environmental exposure unit) to overcome these variations. An ACC is a specially designed room used to expose study participants to a fixed, predetermined allergen concentration for a set period of time. ACCs also allow identical repeated exposures and thus assessment of changes over time in an individual's response.

Briefly, patients eligible were men and women aged between 18 and 50 years with a documented history of moderate-to-severe seasonal grass pollen-related allergic rhinoconjunctivitis for at least the 2 previous pollen seasons. At screening, patients were required to demonstrate grass pollen sensitization through a positive specific skin prick test response (weal diameter >3 mm) to a 5-grass pollen extract (Stallergenes SA) and a specific serum IgE level of at least 0.70 kU/L for timothy grass (assayed with the UniCAP system; Phadia, Uppsala, Sweden). In addition, patients had to show a symptomatic reaction to an allergen challenge test at baseline (i.e., before the administration of any study treatment), which was defined as a Rhinoconjunctivitis Total Symptom Score (RTSS) of at least 7 (of 18) within the 2-hour challenge.

Figure 1:
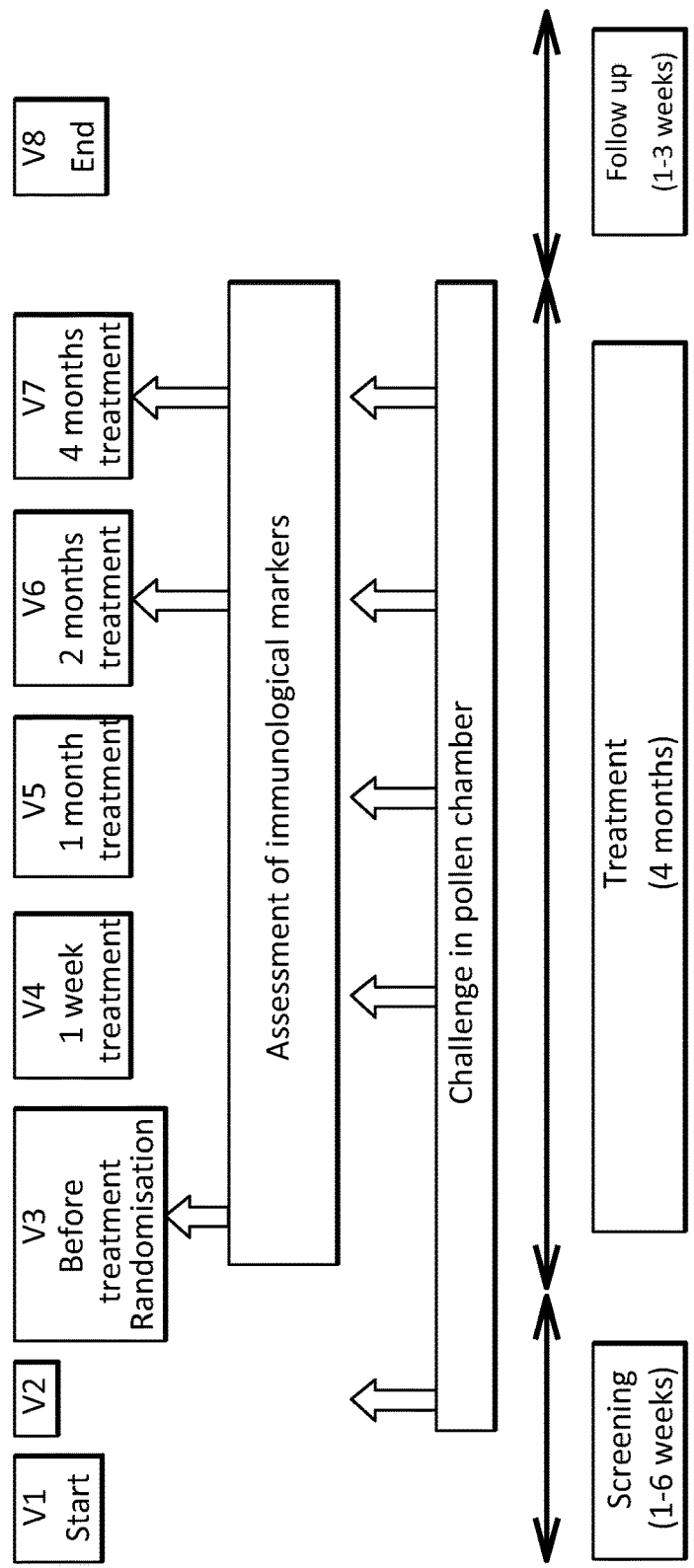
FIG. 1: Study design.

The study was a randomized, double-blind, parallel-group, placebo-controlled, single-center trial, and was conducted outside of pollen season, providing well-controlled allergen exposure. After an initial screening visit and a baseline allergen challenge, eligible patients were randomized 1:1 to receive either a 300-IR SLIT tablet or placebo. Patients underwent an allergen challenge in the chamber with grass pollen before treatment (the baseline challenge). A 2-hour baseline challenge was chosen, which was sufficient for qualification, to avoid unnecessary priming and to keep the patients' burdens as low as possible (no rescue medication was allowed). Additional challenges were performed after 1 week and 1, 2, and 4 months of treatment (each lasting 4 hours) (study design shown in FIG. 1).

The investigational product was a 300-IR 5-grass-pollen SLIT tablet, (orchard, meadow, perennial rye, sweet vernal, and timothy grasses; Stallergènes SA) taken once daily. The IR is a measure of the biological potency of an allergen extract assessed based on skin reactivity. The dosage of the 300-IR tablet corresponded to approximately 20 μg of group 5 major allergens. Patients were told to take the sublingual pollen extract or placebo tablets once a day before eating or drinking and, preferably, at the same time of day throughout the 4-month treatment period.

The measurement of Rhinoconjunctivitis Total Symptom Score (RTSS) before and after sublingual immunotherapy allowed identification of individual responders. The RTSS included the 6 most common symptoms of allergic rhinoconjunctivitis: sneezing, rhinorrhea, nasal pruritus, nasal congestion, ocular pruritus, and tearing. Each symptom was evaluated by the patient with a score ranging from 0 to 3, as follows: 0, absent symptoms (no sign/symptom evident); 1, mild symptom (sign/symptom is clearly present/minimal awareness and easily tolerated); 2, moderate symptom (definite awareness of sign/symptom that is bothersome but tolerable); and 3, severe symptom (sign/symptom that is hard to tolerate and causes interference with daily activities). The RTSS is the sum of the 6 individual symptom scores and thus varies from 0 to 18. The RTSS was recorded every 15 minutes during the 4-hour allergen exposure challenge (2 hours at baseline). The Average Rhinoconjunctivitis Total Symptom Score (ARTSS) for each patient was calculated for each challenge as the average of the RTSSs across the challenge's 16 time points (8 time points for baseline challenge). The primary efficacy variable was the ARTSS during the allergen challenge after 4 months of treatment or at the end point. The secondary efficacy variables were nasal airflow, nasal secretion weight, and cutaneous reactivity. Immunological parameters were exploratory variables.

Example 2: Definition of Clinical Responders

Figure 2:
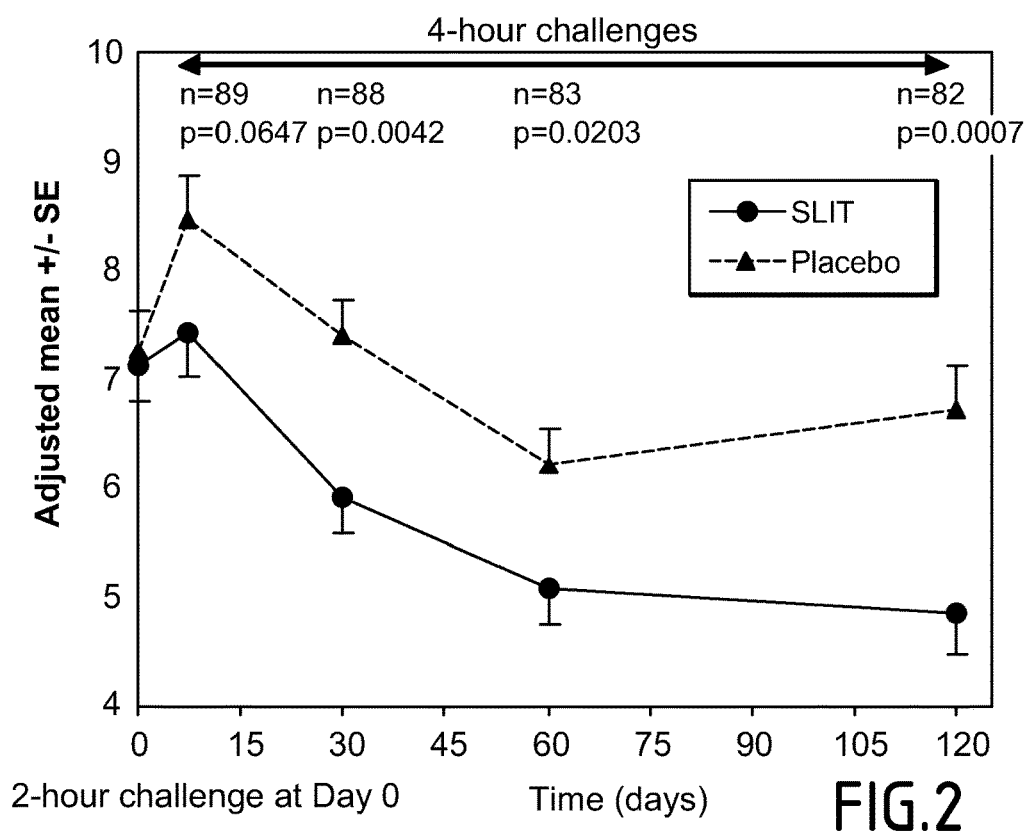
FIG. 2: Results of the study showing improvement in clinical symptoms after SLIT treatment (filled circles) or after placebo treatment (filled triangles). The vertical axis shows the adjusted mean of average Rhinoconjunctivitis Total Symptom Score (RTSS).

As shown in FIG. 2, the study demonstrated a statistically significant reduction in clinical symptoms following at least 1 month of treatment for patients receiving the active grass pollen tablet when compared to the group receiving placebo.

As patients were challenged before treatment (at Visit 2), it was possible to evaluate individual clinical responses by calculating the percentage improvement of Average Rhinoconjunctivitis Total Symptom Score (ARTSS) between the baseline (challenge at V2) and after the last challenge:

(ARTSS at $V2$–ARTSS at last challenge)/ARTSS at $V2 \times 100$.

To analyse potential links between changes in immunological parameters and clinical responses, statistical analyses were pre-defined in the Statistical Analysis Plan (SAP) of the study. The quartiles of % of improvement of ARTSS were calculated for all subjects, active and placebo combined. The third quartile corresponding to at least a 48.9% decrease of ARTSS after treatment was considered as a threshold. Subjects with an ARTSS improvement greater than or equal to the threshold were considered as responders and those lower than the threshold as non-responders. By using the third quartile, 25% of subjects were responders. Thus, immunological results were described using summary statistics for the 4 subgroups (Active Responder: AR, Active Non-Responder: ANR, Placebo Responder: PR, Placebo Non-Responder: PNR) and plotted as individual lines within the 4 subgroups.

Example 3: Analysis of Serum Protein Profiling by 2D-DiGE

Materials and Methods

Protein profiling was performed on sera by 2D-differential gel electrophoresis (2D-DiGE), making no assumption on the identity of potential biomarkers. 2D-DiGE is a technology of 2D gel separation of proteins. The first dimension separates the proteins following their IP (isoelectric point) and the second separates them on their apparent MM (molecular mass).

In DiGE, proteins are visualized by fluorescence after specific chemical labeling with CyDye (Cy3 or Cy5). Different samples to be compared are labeled with different dyes which enable signal detection at different emission wavelengths. The two compared samples are loaded on the same gel. Moreover, the use on each gel of an internal standard composed of all the samples to be compared, in equal amount and labeled with a third Dye (Cy2), enables a more robust gel analysis.

Selection of Samples

Serum samples from 36 patients, collected before (V3) and after treatment (V7), were analyzed. Patients were selected on the basis of their clinical response and their group of treatment.

In a first set of experiments, 16 patients were selected as follows:

The 4 subjects with the largest improvement in the SLIT group: "Active/Most improved" subset.

The 4 subjects with the smallest improvement in the SLIT: "Active/Less improved" subset.

The 4 subjects with the largest improvement in the placebo: "Placebo/Most improved" subset.

The 4 subjects with the smallest improvement in the placebo group: "Placebo/Less improved" subset.

To extend and confirm the results, in a second set of experiments 20 additional patients were analyzed:

8 active patients clinically improved (most of them were "immunoreactive patients"), 4 active patients not clinically improved, 4 placebo patients "clinically improved", and 4 placebo patients "not clinically improved".

Thus, a total of 36 patients were analyzed: 12 "active responders" (AR) and 8 patients from each of the following groups: "active non-responders" (ANR), "placebo responders" (PR) and "placebo non-responders" (PNR).

Serum Sample Processing

Samples were kept at room temperature for 15 minutes and then slowly mixed for 5 minutes.

Serum and plasma are among the most complex media to analyze with proteomic methods due to the wide dynamic range of protein concentrations (spanning over 10 orders of magnitude). Sera were thus depleted of the 14 most abundant proteins for the detection of low-abundant proteins that may be of interest for biomarker identification. Depletion was carried out using Agilent MARS Human-14 spin cartridge, according to manufacturer's protocol. A mobile phase reagent kit for the affinity spin cartridge was used for sample loading, washing and spin-cartridge equilibration (Buffer A, Agilent Ref 5185-5987) and for bound protein elution (Buffer B, Agilent Ref 5185-5988) from the spin cartridge.

Three protein depletions from each crude human serum were pooled into a spin concentrator (5 kDa molecular mass cut-off) and spun at 5000 g for 35 minutes at 10° C. Protein samples were then precipitated with a commercial 2D cleanup kit (GE Healthcare Ref 80-6484-51) according to the manufacturer's protocol and solubilized in a 2D sample solution containing 7M urea, 2M thiourea, 4% Chaps and 30 mM Tris pH 8.8. A standard Bradford assay was performed to determine protein concentration and the sample processing workflow was qualitatively evaluated by SDS-PAGE.

2D-DiGE Analysis

Samples were labeled with CyDye (CyDye DiGE Fluor kit, GE Healthcare), using a ratio of 400 pmoles/50 µg proteins.

Samples collected at V3 and V7 (before and after SLIT, respectively) were analysed. V3 and V7 samples from the same patient were labelled with 2 different fluorochromes loaded onto the same gel. To avoid bias, samples from the different patient groups were distributed across different electrophoresis tanks.

A Cy2 internal standard was obtained by pooling equal amounts of proteins (25 µg) from a first set of experimental samples, and another was generated by pooling equal amounts of proteins (25 µg) from a second set of experimental samples.

Proteins were separated on 24 cm long Immobiline pH 4-7 DryStrip gels (GE Healthcare Ref 17-6002-46) by IEF using the IPGphor system 3. Proteins were focused by increasing the applied voltage up to 10,000 V for a total of 72,750 V·h using the following steps: Phase 1: 50 V-300 V (1 h30); Phase 2: 300 V-3000 V (2 h); Phase 3: 3000 V (2 h30); Phase 4: 3000 V-10,000 V (2 h); Phase 5: 10,000 V (5 h). Strips were then equilibrated in urea-containing buffer (reduction and alkylation) before loading onto SDS polyacrylamide gels (11%) for separation according to molecular mass using an Ettan DALT Six Electrophoresis System (GE Healthcare). DiGE gels were scanned using an Ettan DiGE Imager (GE Healthcare) according to the manufacturer's instructions.

Statistical Analysis

SameSpots 2D gel analysis software (Nonlinear Dynamics) was used to perform quantitative analysis of the differentially expressed proteins. When testing hundreds of proteins for statistical significance with Student's t-test or ANOVA test with only a limited sample size used, many of these proteins may achieve a significant p-value by chance alone. Therefore, expression changes in 2D-DiGE analysis were determined using SameSpots q-value (NonLinear Dynamics; q<0.05).

PCA (Principal Component Analysis) was used as an exploratory tool to investigate the clustering of the proteome datasets, i.e., protein spot volumes from a DiGE gel. The dataset ("y" groups x "n" biological replicates) formed a matrix of protein spot volumes matched across all "y" x "n" gels. As an initial step, PCA was applied to the entire dataset to give an overview of the data structure in order to identify outliers and possible clusters. The most indicative separation was explained by the first principal component (PC1) and the second principal component (PC2) representing the highest percentages of the total variance in the protein spot-matrix. The relative nearness of samples in the plot indicates similarity and large distances between samples indicate dissimilarity in protein expression. Samples could be removed as outliers due to a pattern of variation in the protein spots caused by differences between gels (or protein preparation) rather than differences related to patient group.

Data are expressed as mean±SEM. Statistical differences between groups were assessed using the non-parametric Kruskal-Wallis test. *p-values≤0.05, p-values≤0.01 or *p≤0.001 were considered as significant.

Correlation analyses were performed using the non-parametric Spearman test, where R represents the Spearman correlation coefficient, and ROC analyses were assessed using an empirical model. Statistical and graphical analyses were performed using the Prism5 software (GraphPad).

Significant differences in protein expression changes in 2D-DiGE analysis were assessed using multiple comparison tests, an FDR (False Discovery Rate) adjusted p-value threshold of 0.1, a statistical power >80% and a ≥1.2-fold-change in volume. Statistics on proteomic data were performed using the Samespot program from Nonlinear Dynamics.

Identification of Differentially-Expressed Spots by Mass Spectrometry

Differentially-expressed spots determined by image analysis with SameSpots software were selected for manual spot picking (q<0.05). Preparative gels post-stained with Simply Blue SafeStain (Invitrogen) were used for spot picking. Gel plugs were washed with 200 µL of 100 mM $NH_4HCO_3$/50% ACN for 45 min at 37° C. and then dehydrated in ACN. Each spot was digested with trypsin (50 ng in 5 µL of 25 mM $NH_4HCO_3$/10% ACN, Sigma) at 37° C. overnight, then 6 µL of ACN was added and the mixture was sonicated for 30 min. NanoLC-MS/MS analysis was performed using an Ultimate 3000 RS nano LC system (Dionex) coupled to an ESI-Qq-TOF MS (Maxis) from Bruker Daltonics. $H_2O$/ACN/FA (100/0/0.1 by volume) was used as solvent A and $H_2O$/ACN/FA (20/80/0.1 by volume) as solvent B. Tryptic peptides diluted (1/4, v/v) in 0.1% FA were injected (7 µL) and trapped on an Acclaim PepMap100 (100 µm×2 cm; C18, 5 µm, 100 Å, Dionex) with a flow rate of 12 µL/min. Separation was performed using an Acclaim PepMap RSLC (75 µm×15 cm; C18, 2 µm, 100 Å, Dionex) with a flow rate of 450 nL/min and a linear gradient (5-45% B for 45 min, 45-95% B for 1 min, 95% B for 15 min).

For accurate mass measurements, the lock mass option was enabled in MS mode: m/z 299.2945 (methylstearate, Sigma-Aldrich) and m/z 1221.9906 (chip cube high mass reference, Agilent) ions generated in the electrospray process from ambient air were used for internal recalibration. Nano-LC-MS/MS data were analyzed using the Mascot (Matrix Science, version 2.3) program to search against the human SwissProt (*Homo sapiens*) database assuming trypsin digestion. Precursor mass and fragment mass were searched with initial mass tolerance of 8 ppm and 0.05 Da, respectively and up to 2 miscleavages were allowed for peptide identification. Carbamidomethylation of cysteine residues was specified as a fixed modification. Peptide identifications were accepted if they could be established at a greater than 95% probability as specified by Mascot software.

Trypsin autolysis peaks were excluded. In MS/MS, individual ion scores above 28 indicate identity or extensive homology (p<0.05) and protein scores are derived from ion scores.

Results

Serum Comparisons by 2D-DiGE

Figure 3:
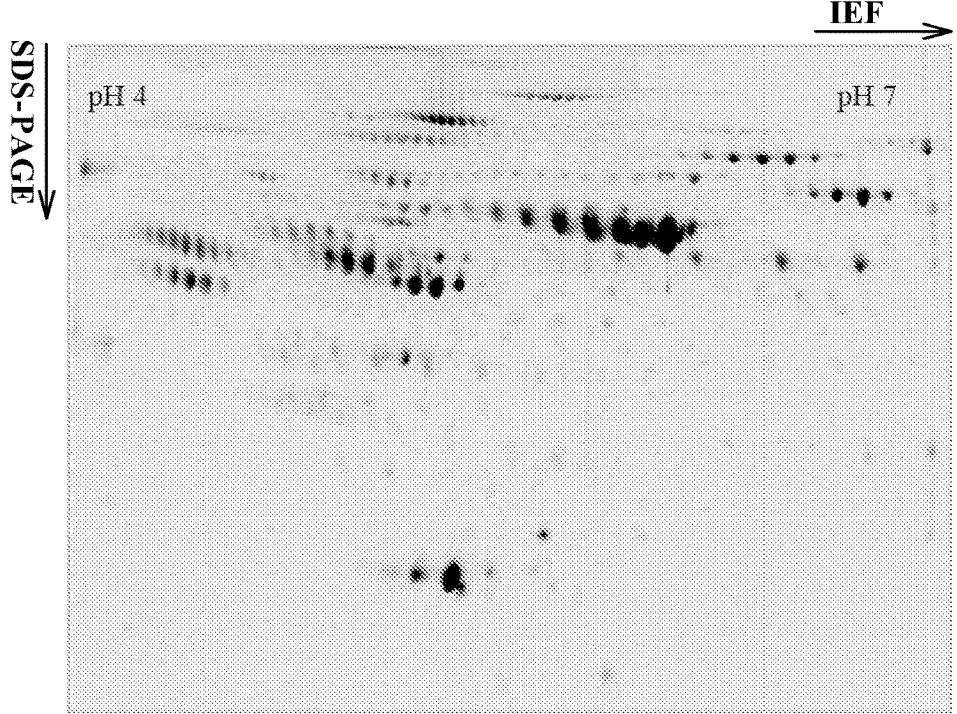
FIG. 3: Typical Cy2 gel image of serum samples. 50 µg of Cy2-labeled proteins were resolved using a pH 4-7 DryStrip gel followed by 11% SDS-PAGE.

The 2D-DiGE analysis enabled comparison between different patient groups (PNR, PR, AR and ANR), but also before (V3) and after (V7) SLIT. The identification of differentially-expressed protein spots was performed by 2D-DiGE followed by mass spectrometry using sera depleted of the 14 most abundant proteins. FIG. 3 shows a typical 2D pattern obtained from such processed sera. A total of 108 gel images were loaded for data analysis using SameSpots software. Images were then categorized into twelve patient groups and a total of 520 spot volumes were compared between groups.

Identification of SLIT Efficacy Predictive Markers (Comparison AR Vs. ANR at V3; AR Group: 12 Patients; ANR Group: 8 Patients)

Figure 4:
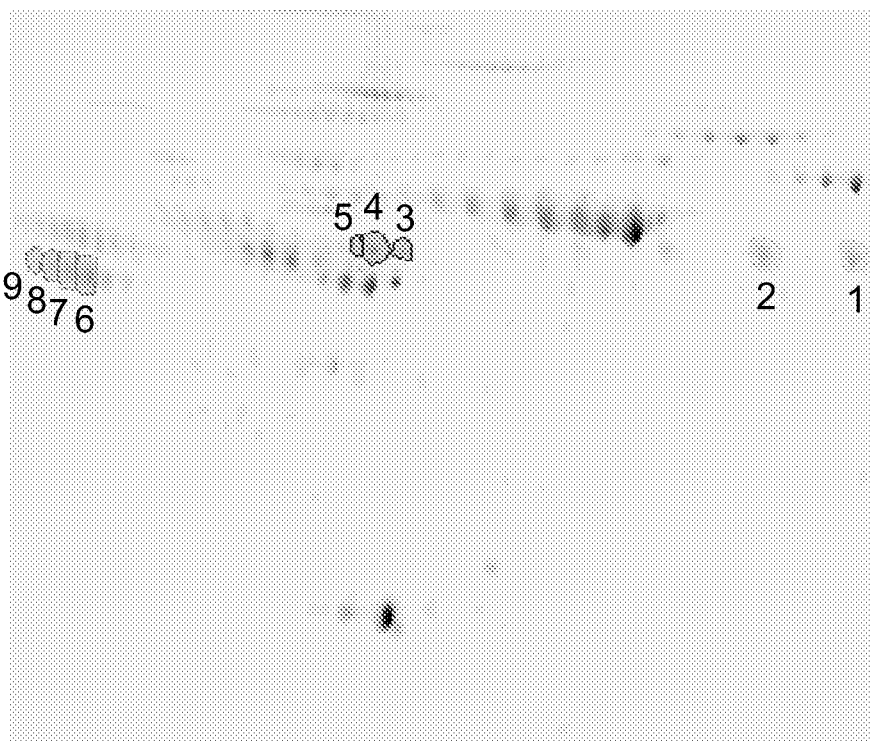
FIG. 4: Protein spots differentially expressed in AR vs. ANR patients at V3 with localization on 2D-gel image. Protein spots (1) to (9) were up-regulated in AR group as compared with ANR group and were identified as β2 glycoprotein 1 (spots 1 and 2), Antithrombin 3 (spots 3 to 5) and Fetuin-A (spots 6 to 9).
Figure 7:
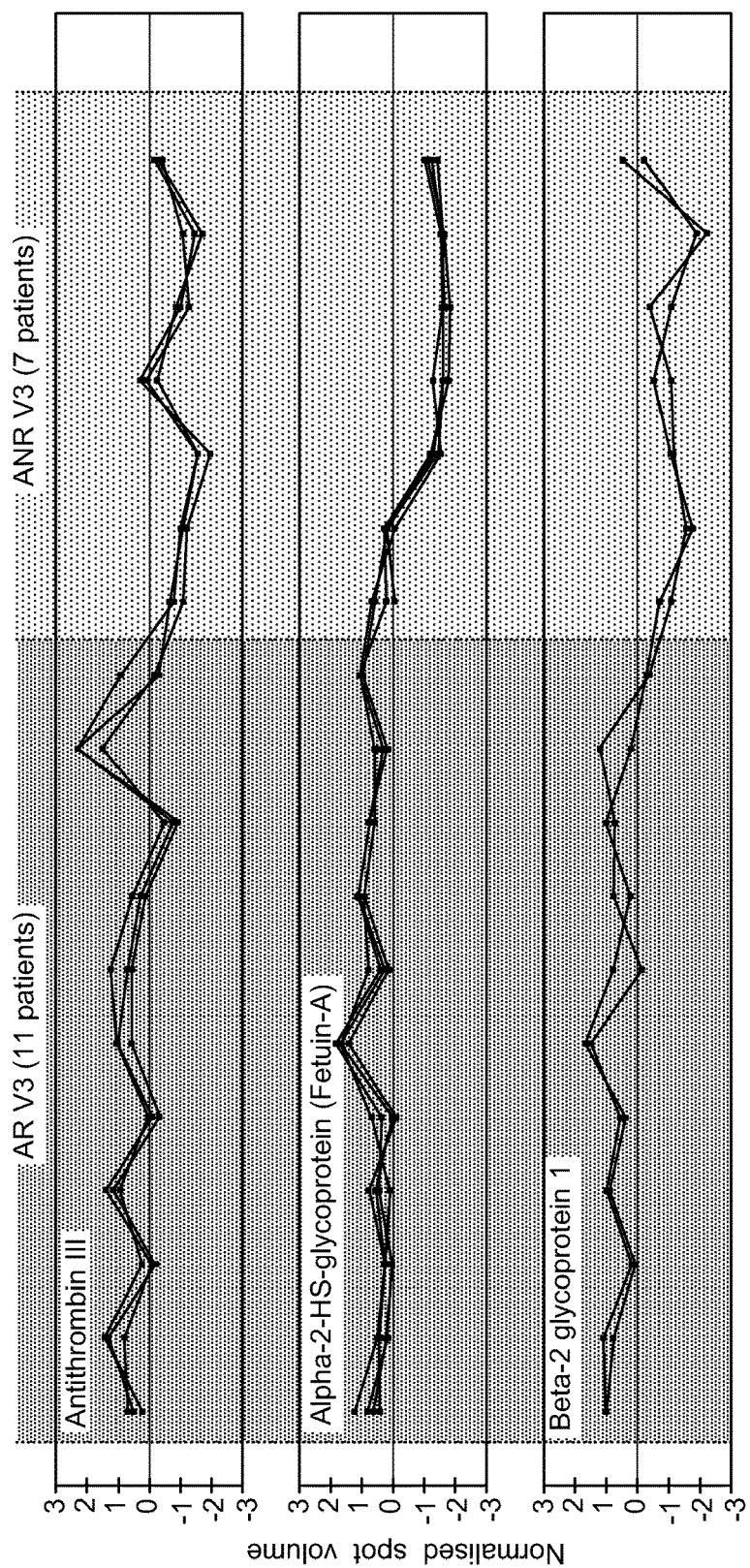
FIG. 7: Normalised spot volume for Antithrombin-III (top), Fetuin-A (middle) and beta-2 glycoprotein 1 (bottom) in AR and ANR patients.

Data analysis using PCA showed two potential outliers (patients 28 from AR and 46 from ANR group) while two distinct clusters representing AR and ANR groups (FIGS. 5 and 6) were established. Nine protein spots were up-regulated in the AR group and identified as beta-2-glycoprotein 1 (spots 1 and 2), Antithrombin-III (spots 3 to 5) and Fetuin-A (spots 6 to 9) (FIGS. 4 and 7).

In order to confirm the results obtained by 2D-DiGE, quantitative measurements of the candidate biomarker proteins identified by 2D-DiGE were performed in plasma samples with commercial kits. The measurements were carried out on the specific proteins identified in the 2D-DiGE experiments. They were also carried out on a range of inflammation-related proteins, as the results of the 2D-DiGE experiments suggested that inflammation-related proteins may represent suitable markers.

Commercial ELISA kits were used to quantify proteins in patients' plasma samples collected before treatment (V3). The following kits were used, according to the manufacturer's instructions: Fetuin-A (AHSG) Human ELISA kit, BioVendor, reference RD191037100; Human Fetuin-A ELISA kit, Epitope Diagnostics, reference KT-800; Human Beta-2 Glycoprotein 1 ELISA kit, Bethyl Laboratories, reference E88-142; Antithrombin A (AT-3) ELISA kit, Antibodies Online, reference ABIN365872; and Human transferrin ELISA kit, Bethyl Laboratories, reference E88-128. MCP-1 and Eotaxin were measured using a CBA Flex kit (BD Biosciences, CA, USA) according to the manufacturer's instructions. All patients were tested in a blinded manner with each ELISA assay (n=82).

Figure 8:
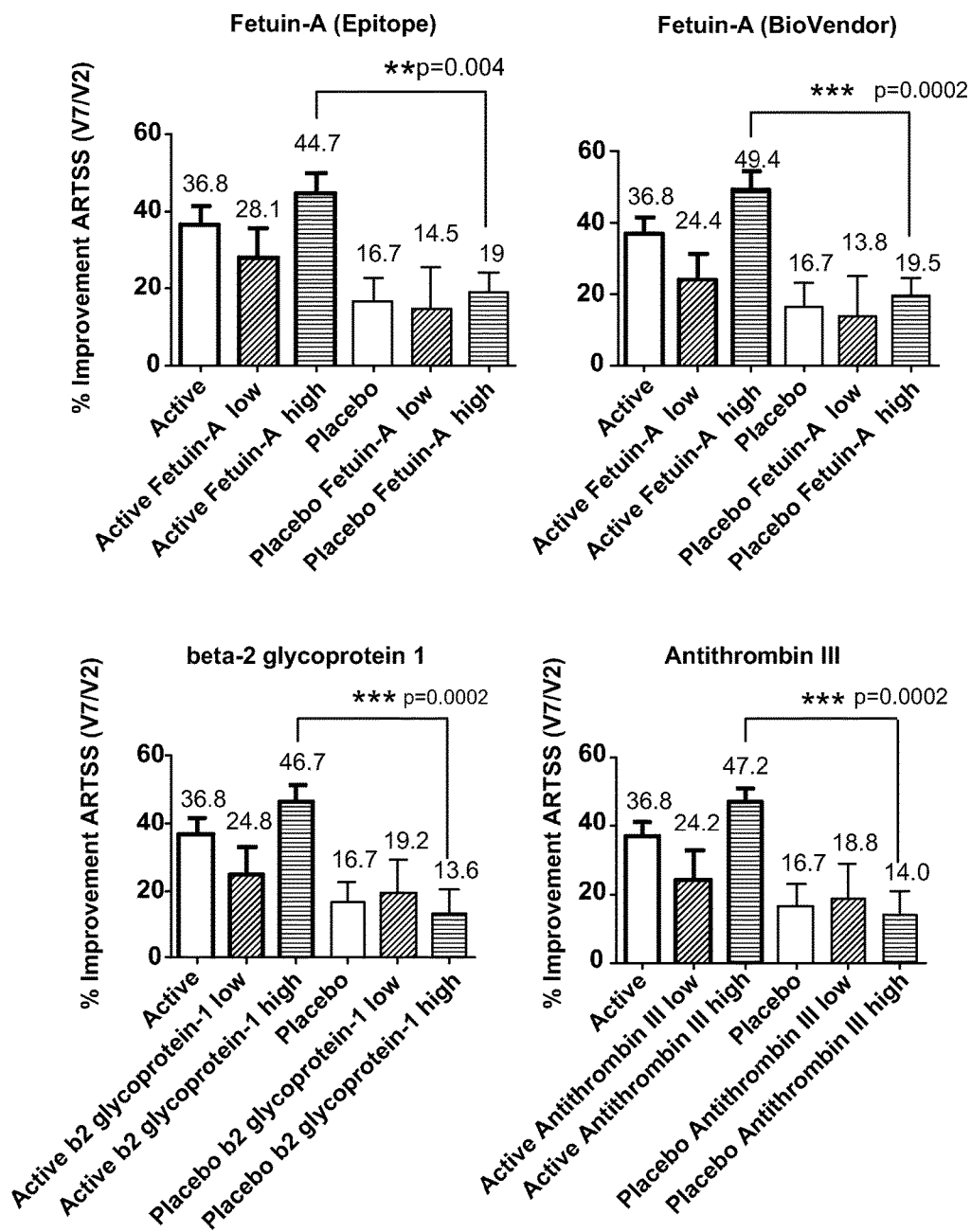
FIG. 8: Clinical improvement in subgroups of patients defined on the basis of their low or high plasmatic expression of candidate biomarkers before treatment. Results shown for Fetuin-A (top), beta2-glycoprotein 1 (bottom left) and Antithrombin-III (bottom right).
Figure 10:
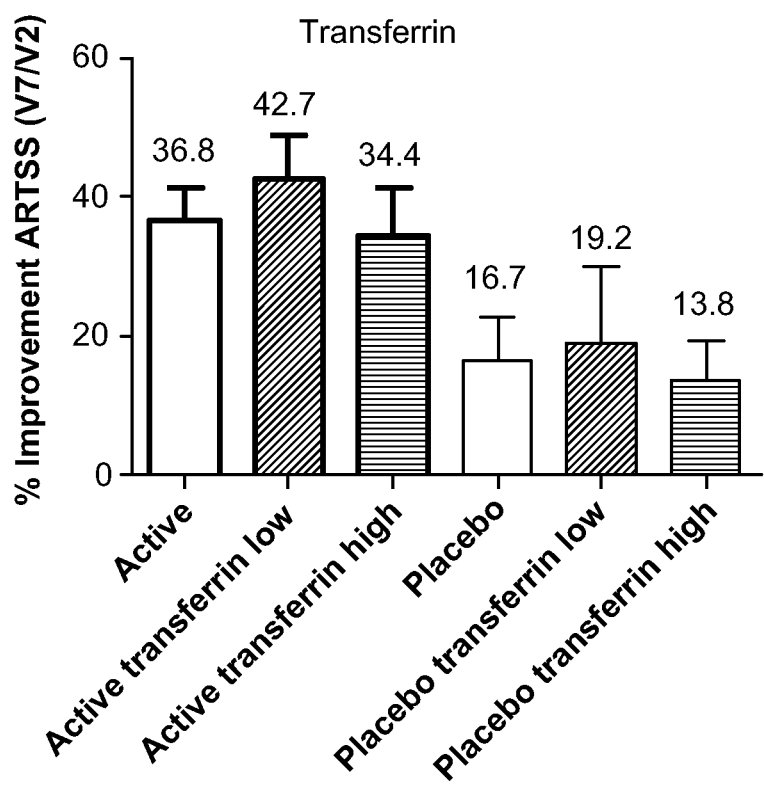
FIG. 10: Clinical improvement in subgroups of patients defined on the basis of their low or high plasmatic expression of a randomly selected control protein (transferrin).

To analyse these results, patients from each treatment group (i.e., active and placebo) were divided into 2 equal subgroups depending upon levels of each of the candidate markers found in their plasma before treatment (subgroup "low" and "high", with protein levels respectively < or > to the median value for each marker considered). As shown in FIGS. 8 and 9, a more pronounced improvement in clinical symptoms was always observed in active patients who had high marker levels. No such correlation was seen in other proteins, such as transferrin: there was no difference in clinical response between active patients who had low or high levels of plasmatic transferrin (FIG. 10). Thus, there were higher differences between active "high" versus placebo "high" patients than between all active versus all placebo patients. Thus, if patients had been selected before treatment on the basis of expression of these biomarker candidates, we could show a better clinical efficacy of SLIT treatment in those 50% active patients with the highest marker levels in their plasmas. No such differences were observed in the placebo group.

In conclusion, this proteomic approach enabled the identification of different proteins overexpressed in active responder patients before SLIT (Fetuin-A, beta-2 glycoprotein 1, Antithrombin-III, MCP-1 and Eotaxin). These proteins are considered as candidate serum biomarkers.

The proteins overexpressed, prior to SLIT, in the sera of patients who demonstrated greater improvement in clinical symptoms in response to SLIT treatment thus represent predictive biomarkers which can be used in the selection of patients more likely to respond to SLIT.

Identification of Specific Fetuin-A Isoforms by Mass Spectrometry

Figure 16:
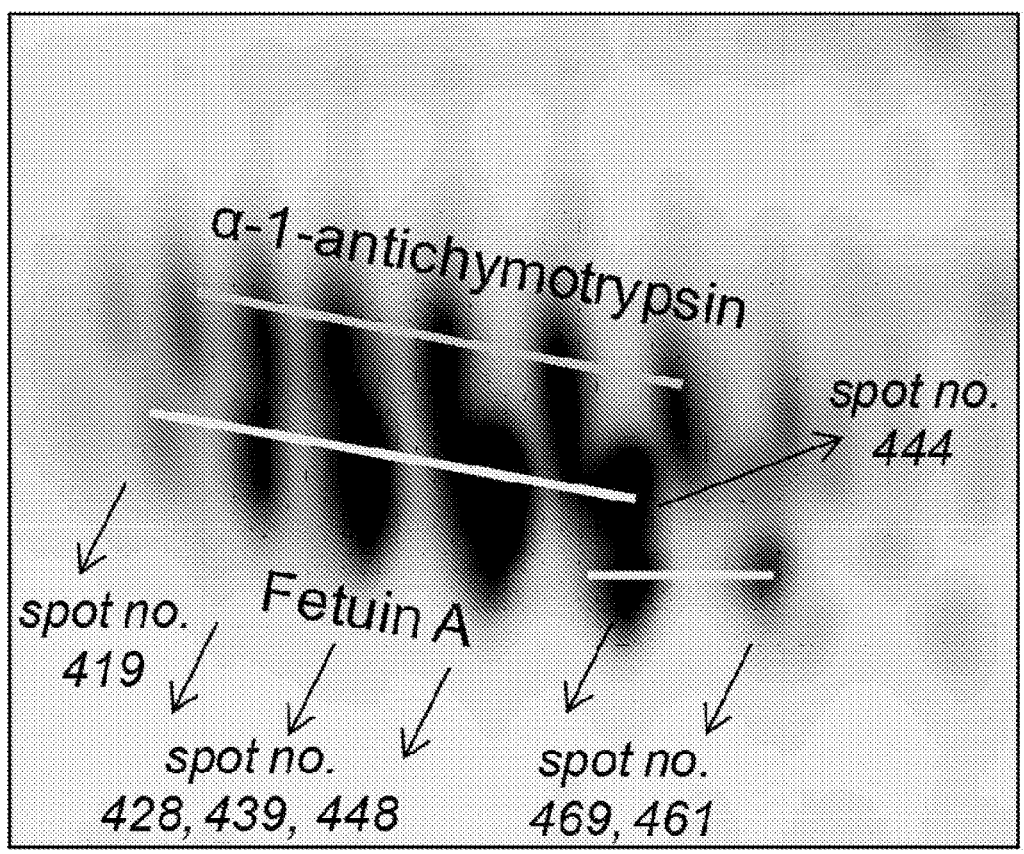
FIG. 16: Representative image with localization of Fetuin-A protein spots.

As shown in FIG. 16, different protein spots corresponding to Fetuin-A could be observed by 2D-DIGE. Among these spots, 6 protein spots (spots 428/439/448 and 444/469/461) were identified by mass spectrometry as α-2-HS-glycoprotein or Fetuin-A (see Table 1, below). These protein spots probably correspond to different Fetuin-A isoforms. A difference in the amount of glycosylation or phosphorylation may induce the observed shift of the Fetuin-A isoelectric point.

TABLE 1

LS/MS identification of spots as Fetuin A isoforms

| Spot no./ Picking no. | MALDI-TOF-MS Accession | LC-MS/MS Accession | Modifications (Carbamidomethylation C:) | m/z meas. | z | Δ m/z [ppm] | Rt [min] | Scores | P | Range | Sequence |
|---|---|---|---|---|---|---|---|---|---|---|---|
| 419/A1 | ni | ni | ni | ni | ni | ni | ni | ni | ni | ni | ni |
| 428/A2 | FETUA_HUMAN | FETUA_HUMAN |  | 432.74420 | 2 | -1.64 | 25.00 | 19.4 | 0 | 179-185 | K.LINDYVK.N (SEQ ID NO: 6) |
|  |  |  |  | 480.75780 | 2 | -2.66 | 25.11 | 66.9 | 0 | 341-350 | K.ADLSGITGAR.N (SEQ ID NO: 7) |
|  |  |  |  | 487.26960 | 2 | 0.65 | 31.91 | 42.1 | 0 | 145-152 | K.EQLSLLDR.F (SEQ ID NO: 8) |
|  |  |  |  | 531.29810 | 2 | 1.12 | 37.09 | 19.6 | 0 | 307-315 | R.EIGELYLPK.F (SEQ ID NO: 9) |
|  |  |  |  | 547.81830 | 2 | -2.14 | 22.58 | 13.7 | 0 | 351-360 | R.NLAVSQVVHK.A (SEQ ID NO: 10) |
|  |  |  | C: 8 | 554.25700 | 3 | -4.27 | 33.61 | 24.2 | 0 | 107-120 | K.EHAVEGDCDFQLLK.L (SEQ ID NO: 11) |
|  |  |  |  | 608.36990 | 2 | 1.49 | 48.17 | 18.3 | 0 | 380-390 | K.ITLLSALVETR.T (SEQ ID NO: 12) |
| 439/A3 | FETUA_HUMAN | FETUA_HUMAN |  | 407.22990 | 2 | 2.46 | 26.72 | 48.4 | 0 | 125-131 | K.FSVVYAK.C (SEQ ID NO: 13) |
|  |  |  | C: 11 | 508.25480 | 4 | -1.86 | 32.00 | 15.8 | 1 | 104-120 | R.QLKEHAVEGDCDFQLLK.L (SEQ ID NO: 14) |
|  |  |  | C: 8 | 554.25990 | 3 | 0.96 | 33.45 | 110.2 | 0 | 107-120 | K.EHAVEGDCDFQLLK.L (SEQ ID NO: 11) |
|  |  |  |  | 613.84320 | 2 | 0.96 | 29.06 | 32.7 | 1 | 121-131 | K.LDGKFSVVYAK.C (SEQ ID NO: 15) |
|  |  |  | C: 11 | 677.33900 | 3 | 0.64 | 32.09 | 57.3 | 1 | 104-120 | R.QLKEHAVEGDCDFQLLK.L (SEQ ID NO: 14) |
|  |  |  |  | 694.34340 | 3 | -3.67 | 34.32 | 22.9 | 0 | 318-337 | R.HTFMGVVSLGSPSGEVSHPR.K (SEQ ID NO: 16) |

TABLE 1-continued

LS/MS identification of spots as Fetuin A isoforms

| Spot no./ Picking no. | MALDI-TOF-MS Accession | LC-MS/MS Accession | Modifications (Carbamidomethylation C:) | m/z meas. | z | Δ m/z [ppm] | Rt [min] | Scores | P | Range | Sequence |
|---|---|---|---|---|---|---|---|---|---|---|---|
| 448/A4 | FETUA_HU | FETUA_HU | | 407.22820 | 2 | −1.71 | 26.92 | 50.2 | 0 | 125-131 | K.FSVVYAK.C (SEQ ID NO: 13) |
| | | | | 521.01110 | 4 | −0.34 | 34.34 | 57.6 | 0 | 318-337 | R.HTFMGVVSLG SPSGEVSHPR.K (SEQ ID NO: 16) |
| | | | C: 8 | 554.25930 | 3 | −0.12 | 33.59 | 102.0 | 0 | 107-120 | K.EHAVEGDCDF QLLK.L(SEQ ID NO:11) |
| | | | | 613.84280 | 2 | 0.30 | 29.11 | 37.9 | 1 | 121-131 | K.LDGKFSVVYAK .C (SEQ ID NO: 15) |
| | | | C: 11 | 677.33820 | 3 | −0.54 | 32.22 | 54.5 | 1 | 104-120 | R.QLKEHAVEGD CDFQLLK.L (SEQ ID NO: 14) |
| 444/A5 | FETUA_HU MAN | FETUA_HU MAN | C: 11 | 407.22920 | 2 | 0.75 | 26.74 | 48.4 | 0 | 125-131 | K.FSVVYAK.C (SEQ ID NO: 13) |
| | | | | 409.56340 | 3 | −1.87 | 28.95 | 39.0 | 1 | 121-131 | K.LDGKFSVVYAK .C (SEQ ID NO: 15) |
| | | | C: 11 | 508.25520 | 4 | −1.07 | 32.10 | 34.6 | 1 | 104-120 | R.QLKEHAVEGD CDFQLLK.L (SEQ ID NO: 14 |
| | | | | 521.01010 | 4 | −2.26 | 34.21 | 28.3 | 0 | 318-337 | R.HTFMGVVSLG SPSGEVSHPR.K (SEQ ID NO: 16) |
| | | | C: 8 | 554.25890 | 3 | −0.84 | 33.37 | 82.5 | 0 | 107-120 | K.EHAVEGDCDF QLLK.L (SEQ ID NO: 11) |
| 469/A6 | FETUA_HU MAN | FETUA_HU MAN | | 407.22900 | 2 | 0.25 | 27.12 | 46.4 | 0 | 125-131 | K.FSVVYAK.C (SEQ ID NO: 13) |
| | | | C: 8 | 554.25940 | 3 | 0.06 | 33.53 | 70.1 | 0 | 107-120 | K.EHAVEGDCDF QLLK.L (SEQ ID NO: 11) |
| 461/A7 | ni | FETUA_HU MAN | | 407.22890 | 2 | 0.01 | 26.76 | 55.7 | 0 | 125-131 | K.FSVVYAK.C (SEQ ID NO: 13) |
| | | | C: 8 | 554.25870 | 3 | −1.20 | 33.51 | 63.3 | 0 | 107-120 | K.EHAVEGDCDF QLLK.L (SEQ ID NO: 11) |
| | | | | 527.79680 | 2 | −2.66 | 25.80 | 24.6 | 0 | 89-97 | K.LPNNVLQEK.I (SEQ ID NO: 17) |
| | | | | 530.94560 | 3 | −3.28 | 49.14 | 17.4 | 0 | 156-168 | R.ESLLNHFLYEV AR.R (SEQ ID NO: 18) |
| | | | | 811.85030 | 2 | −4.28 | 29.00 | 21.9 | 0 | 583-596 | K.AESPEVCFNE ESPK.I (SEQ ID NO: 19) |

Figure 17:
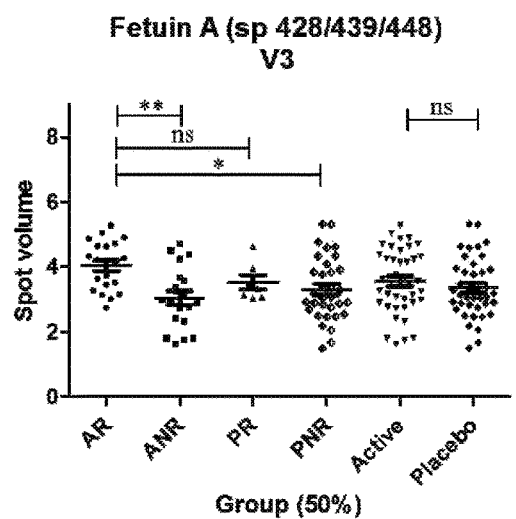
FIG. 17: Expression levels of Fetuin-A protein spots 428/439/448 by DiGE in sera from grass pollen allergic patients before AIT. Fetuin-A spot volumes in sera from patients in the active group in comparison to the placebo group or in clinical responders versus non-responders (% ARTSS improvement ≥43.9 and ≤43.9, respectively) (*p-value≤0.05, **p≤0.01, Kruskal-Wallis test). (AR: active responders, n=21; ANR: active non-responders, n=20; PR: placebo responders, n=7; PNR: placebo non-responders, n=33). Mean±SEM are presented.

Pertinence of Fetuin-A Isoforms Corresponding to Spots 428/439/448 as Candidate AIT Positive Response Markers To screen differentially-expressed proteins, sera from allergic patients (n=82) were analyzed by 2D-DIGE. The expression of Fetuin-A in these spots was significantly increased in sera from patients in the active responder (AR) group in comparison to the active non-responder (ANR) group (difference statistically significant using the Kruskal-Wallis test, FIG. 17). This analysis therefore indicated that Fetuin-A is a candidate positive AIT response marker.

Figure 18:
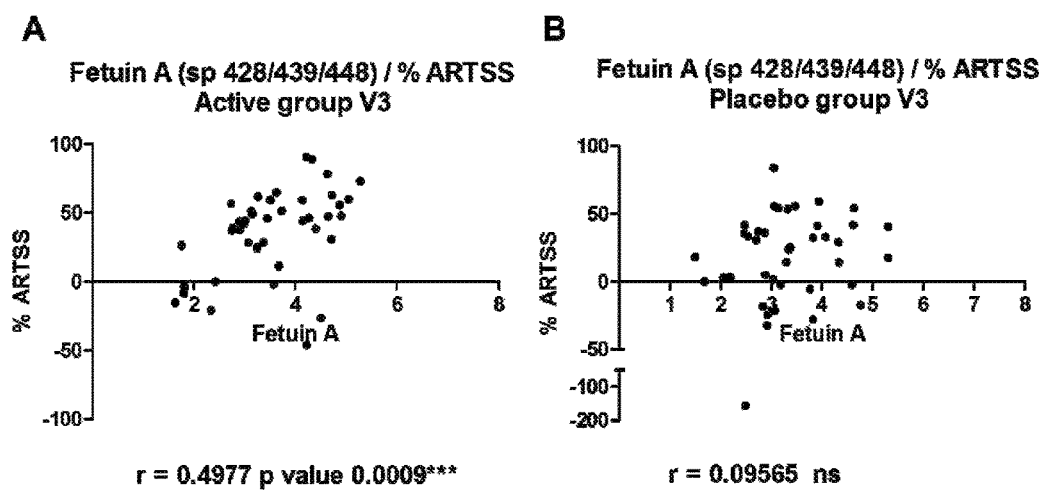
FIG. 18: Correlation of protein levels of Fetuin-A spots 428/439/448 levels with % of ARTSS in sera from grass pollen allergic patients before AIT. Spearman correlation of Fetuin-A expression with % of ARTSS improvement in patients from active (A) and placebo (B) groups before AIT.

The relationship between expression levels of Fetuin-A and the clinical benefit of AIT was evaluated by a Spearman correlation test. When plotted against percentages of ARTSS improvement for each individual patient (FIGS. 18-19), Fetuin-A spots 428/439/448 expression levels were significantly correlated with clinical benefit in patients from the active group (with Spearman correlation of r=0.497, p=0.0009), whereas no such correlation was observed in placebo-treated patients (r=0.095). These results suggest that Fetuin-A may be used as a serum marker for prediction of AIT positive response.

Figure 19:
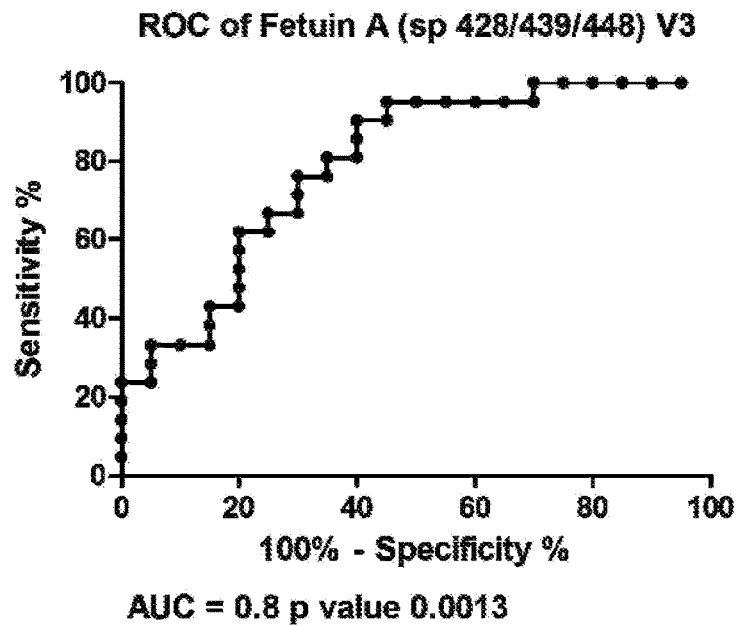
FIG. 19: ROC curve of protein levels of Fetuin-A spots 428/439/448 of 21 active responders and 20 active non-responders. (AUC: area under the ROC curve).

The pertinence of Fetuin-A was further assessed by a receiver operating characteristic (ROC) analysis. The ROC curve is a useful method for evaluating clinical usefulness of a biomarker and for comparing the effectiveness between different biomarkers. A larger area under the ROC curve (AUC) generally represents more reliability and better discrimination. The ROC curve of Fetuin-A levels of 21 active responders and 20 active non-responders is shown in FIG. 19. The AUC was of 0.8 (with p-value of 0.0013), confirming that Fetuin-A is useful to discriminate clinical responders from non-responders before AIT.

Figure 21:
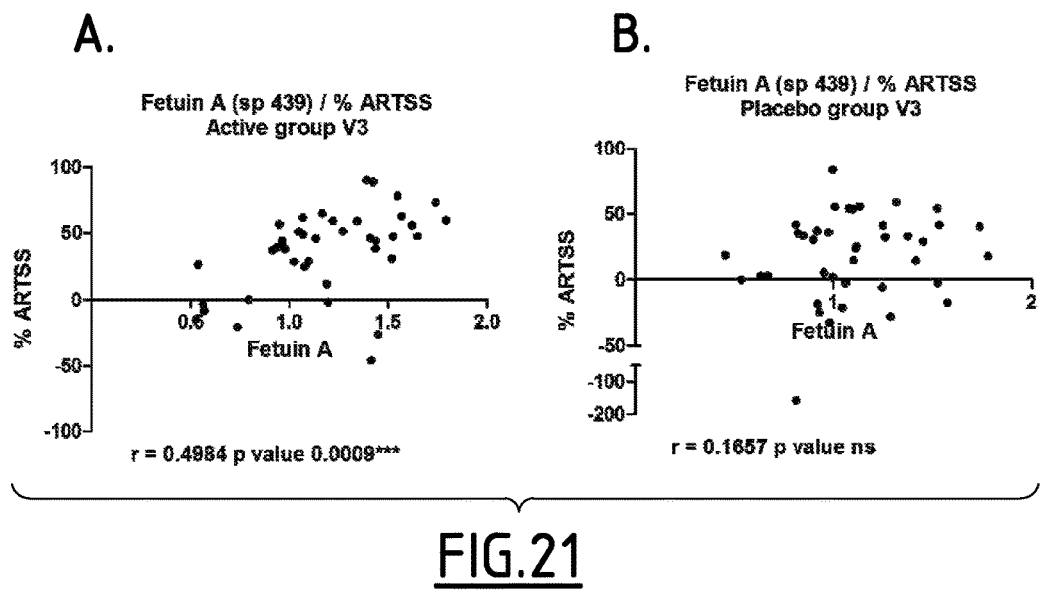
FIG. 21: Spearman correlation of protein levels of Fetuin-A spot 439 with % of ARTSS improvement in patients from active (A) and placebo (B) groups before treatment.

Furthermore, the relationship between expression levels of a specific isoform of Fetuin-A (corresponding to spot 439) and the clinical benefit of AIT was evaluated by a Spearman correlation test. When plotted against percentages of ARTSS improvement for each individual patient (FIG. 21), Fetuin-A spot 439 expression levels were significantly correlated with clinical benefit in patients from the active group (with Spearman correlation of r=0.4984, p=0.0009), whereas no such correlation was observed in placebo-treated patients (r=0.1657). These results suggest that the specific isoform of Fetuin-A corresponding to spot 439 may in particular be used as a serum marker for prediction of AIT positive response.

Figure 22:
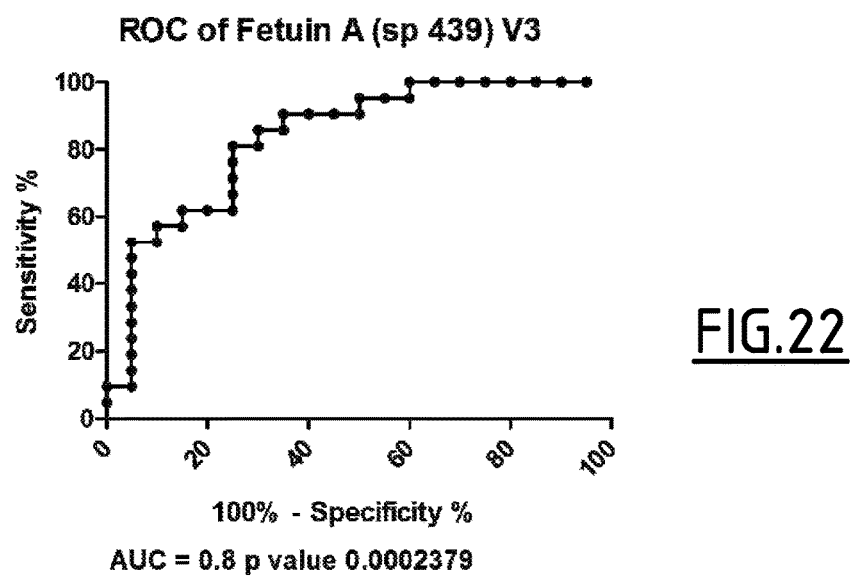
FIG. 22: ROC curve of protein levels of Fetuin-A spot 439 of 21 active responders and 20 active non-responders. (AUC: area under the ROC curve).

The pertinence of Fetuin-A spot 439 was further assessed by a receiver operating characteristic (ROC) analysis. The ROC curve of Fetuin-A spot 439 levels is shown in FIG. 22. The AUC was of 0.8 (with p-value of 0.0002379), confirming that Fetuin-A spot 439 is useful to discriminate clinical responders from non-responders before AIT.

Further Validation of Fetuin-A as a Candidate Biomarker by ELISA

Figure 20:
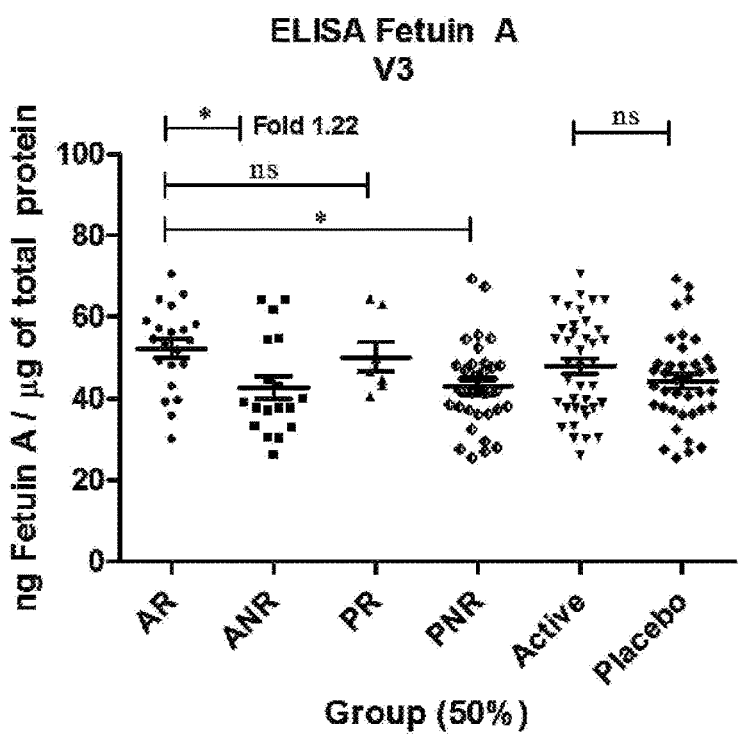
FIG. 20: Determination of Fetuin-A protein levels by ELISA in sera from grass pollen allergic patients before AIT. Expression of Fetuin-A in sera from patients in the active group in comparison to the placebo group or in clinical responders versus non-responders (% ARTSS improvement ≥43.9 and <43.9, respectively) (Kruskal-Wallis test). (AR: active responders, n=21; ANR: active non-responders, n=20; PR: placebo responders, n=7; PNR: placebo non responders, n=33). Mean±SEM are presented.

The expression of Fetuin A, identified through the 2D-DiGE approach, was thus assessed in the 82 serum samples by ELISA using commercial kits. Out of those experiments, the inventors validated Fetuin-A protein as differentially-represented between active responder (AR) and active non-responder (ANR) groups (FIG. 20).

In conclusion, Fetuin-A was proved as a candidate serum biomarker for prediction of AIT positive response. Fetuin-A was observed as differentially-represented between active responder (AR, n=21) and active non-responder (ANR, n=20). Importantly, differences in Fetuin-A isoelectric points were observed for such candidate biomarkers and the expression levels of three Fetuin-A isoforms were significantly correlated with clinical benefit in patients from the active group, whereas no such correlation was observed in placebo-treated patients.

Identification of a Phosphorylated Peptide in Fetuin-A Isoforms

Figure 23:
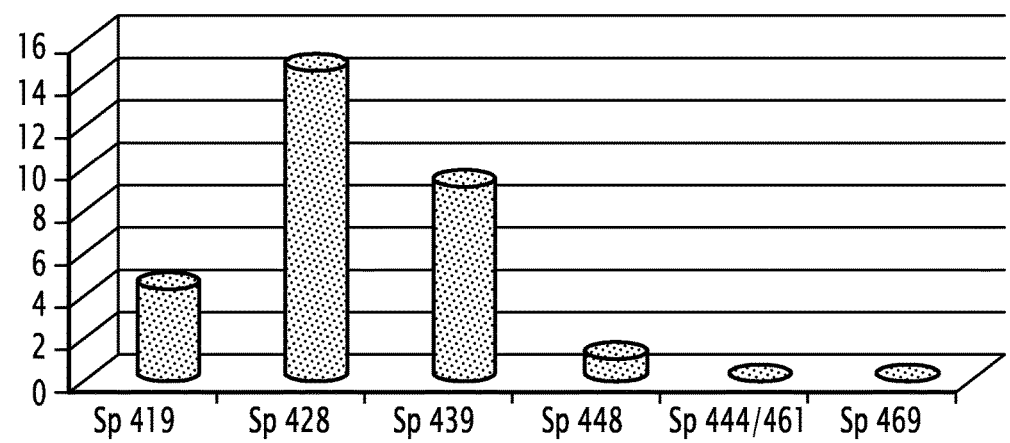
FIG. 23: Abundance of Fetuin-A peptide His318-Arg337 phosphorylated on Ser330 in the Fetuin-A spots shown in FIG. 16. The y axis shows the ratio of phosphorylated to total peptide [P/(P+NP)]. The ratio for spot 419 may be an underestimation due to low abundance of protein on the gel.

Fetuin-A isoform spots were excised using an ExQuest robot (BioRad), digested with trypsin and analysed by LC-MS/MS (Maxis 4G, Bruker) before biocomputing analysis (LCMS ProGenosis software, Nonlinear Dynamics). A phosphorylated peptide corresponding to a tryptic peptide of Fetuin-A (His318-Arg 337 of SEQ ID NO: 1) was detected, which was phosphorylated on the residue corresponding to Ser 330 of SEQ ID NO: 1. The peptide was found to be most abundant in acidic Fetuin-A isoforms and less abundant or undetectable in basic fetuin isoforms (FIG. 23). Thus, detection of the phosphorylated peptide has potential as a specific marker of the fetuin isoforms of interest and as a marker of AIT efficacy in itself.

The invention claimed is:

1. A method of predicting responsiveness of a patient allergic to an allergen, to an immunotherapy with said allergen, and treating the allergic patient, the method comprising the steps of:
   a) detecting the level of expression of acidic Fetuin-A isoforms in a biological sample from said allergic patient, said acidic Fetuin-A isoforms having a pI of 4.5 to 4.7;
   b) comparing the expression level of said acidic Fetuin-A isoforms having a pI of 4.5 to 4.7 with a control;
   c) determining that said allergic patient is likely to be a responder or non-responder to immunotherapy with said allergen based on the comparison with the control; and
   d) administering to said allergic patient likely to be the responder to the immunotherapy, the immunotherapy with the allergen to reduce immune response, wherein:
   (i) the control is derived from a responder allergic subject or a group of responder allergic subjects known to respond to said immunotherapy, and it is determined that the allergic patient is likely to be the responder to the immunotherapy if the level of expression of said acidic isoform of Fetuin A having a pI of 4.5 to 4.7 in the biological sample from said allergic patient is equal to or greater than the level of expression detected in the control; or
   (ii) the control is derived from a non-responder allergic subject or a group of non-responder allergic subjects, and it is determined that the allergic patient is likely to be the responder to immunotherapy if the level of expression of said acidic isoforms of Fetuin A in the biological sample from said allergic patient is greater than the level of expression detected in the control sample.

2. A method of predicting responsiveness of a patient allergic to an allergen, to an immunotherapy with said allergen, and treating the allergic patient, the method comprising the steps of:
   a) detecting the level of expression of a phosphorylated isoform of Fetuin-A which is phosphorylated on the serine corresponding to Ser330 of SEQ ID NO: 1, in a biological sample from said allergic patient;
   b) comparing said level of expression of phosphorylated isoform of Fetuin-A which is phosphorylated on the serine corresponding to Ser330 of SEQ ID NO: 1 with a control;
   c) determining that said allergic patient is likely to be a responder or non-responder to immunotherapy with said allergen based on the comparison with the control; and
   d) administering to said allergic patient likely to be the responder to the immunotherapy, the immunotherapy with the allergen to reduce immune response;
   wherein:
   (i) the control is derived from a responder allergic subject or a group of responder allergic subjects known to respond to said immunotherapy, and it is determined that the allergic patient is likely to be the responder to the immunotherapy if the level of expression of said phosphorylated isoform of Fetuin A which is phosphorylated on the serine corresponding to Ser330 of SEQ ID NO: 1 in the biological sample from said allergic patient is equal to or greater than the level of expression detected in the control; or
   (ii) the control is derived from a non-responder allergic subject or a group of non-responder allergic subjects, and it is determined that the allergic patient is likely to be the responder to immunotherapy if the level of expression of said phosphorylated isoform of Fetuin A which is phosphorylated on the serine corresponding to Ser330 of SEQ ID NO: 1 in the biological sample from said allergic patient is greater than the level of expression detected in the control sample.

3. A method of selecting a patient allergic to an allergen for an immunotherapy with said allergen and treating the selected allergic patient with the immunotherapy, the method comprising the steps of:
   a) detecting the level of expression of a phosphorylated isoform of Fetuin-A which is phosphorylated on the serine corresponding to Ser330 of SEQ ID NO: 1, in a biological sample from said allergic patient;
   b) comparing said level of expression of phosphorylated isoform of Fetuin A which is phosphorylated on the serine corresponding to Ser330 of SEQ ID NO: 1 Fetuin A with a control;
   c) selecting or rejecting said allergic patient for immunotherapy based on the comparison with the control; and
   d) administering to said selected allergic patient, the immunotherapy with the allergen to reduce immune response;
   wherein said biological sample is taken before the commencement of the immunotherapy, and wherein:
   (i) the control is derived from a responder allergic subject or a group of responder allergic subjects known to respond to said immunotherapy, and it is determined that the allergic patient is likely to be the responder to the immunotherapy if the level of expression of said phosphorylated isoform of Fetuin A which is phosphorylated on the serine corresponding to Ser330 of SEQ ID NO: 1 in the biological sample from said allergic patient is equal to or greater than the level of expression detected in the control; or (ii) the control is derived from a non-responder allergic subject or a group of non-responder allergic subjects, and it is determined that the allergic patient is likely to be the responder to immunotherapy if the level of expression of said phosphorylated isoform of Fetuin A which is phosphorylated on the serine corresponding to Ser330 of SEQ ID NO: 1 in the biological sample from said allergic patient is greater than the level of expression detected in the control sample.

4. The method according to claim 3, wherein the allergic patient has grass pollen allergy.

5. The method according to claim 3, wherein the allergic patient has allergy to pollen from one or more of *Dactylis, Poa, Lolium, Anthoxanthum* and *Phleum* genera.

6. The method according to claim 3, wherein the immunotherapy comprises administration of allergen to a mucosal surface, optionally a sublingual, oral, buccal, ocular, rectal, urinal, pulmonal or otolar surface, or administration via a subcutaneous, intranasal, transdermal or intralymphatic route.

7. The method according to claim 6, wherein said immunotherapy comprises administration of grass pollen extract from one or more of *Dactylis, Poa, Lolium, Anthoxanthum* and *Phleum* genera.

8. The method according to claim 2, wherein the allergic patient has grass pollen allergy.

9. The method according to claim 2, wherein the allergic patient has allergy to pollen from one or more of *Dactylis, Poa, Lolium, Anthoxanthum* and *Phleum* genera.

10. The method according to claim 2, wherein the immunotherapy comprises administration of allergen to a mucosal surface, optionally a sublingual, oral, buccal, ocular, rectal, urinal, pulmonal or otolar surface, or administration via a subcutaneous, intranasal, transdermal or intralymphatic route.

11. The method according to claim 10, wherein said immunotherapy comprises administration of grass pollen extract from one or more of *Dactylis, Poa, Lolium, Anthoxanthum* and *Phleum* genera.

12. The method according to claim 1, wherein the allergic patient has grass pollen allergy.

13. The method according to claim 1, wherein the allergic patient has allergy to pollen from one or more of *Dactylis, Poa, Lolium, Anthoxanthum* and *Phleum* genera.

14. The method according to claim 1, wherein the immunotherapy comprises administration of allergen to a mucosal surface, optionally a sublingual, oral, buccal, ocular, rectal, urinal, pulmonal or otolar surface, or administration via a subcutaneous, intranasal, transdermal or intralymphatic route.

15. The method according to claim 14, wherein said immunotherapy comprises administration of grass pollen extract from one or more of *Dactylis, Poa, Lolium, Anthoxanthum* and *Phleum* genera.

16. The method according to claim 1, wherein said immunotherapy comprises administration of grass pollen extract from one or more of *Dactylis, Poa, Lolium, Anthoxanthum* and *Phleum* genera.

* * * * *

UNITED STATES PATENT AND TRADEMARK OFFICE
CERTIFICATE OF CORRECTION

PATENT NO. : 10,101,341 B2  
APPLICATION NO. : 14/110242  
DATED : October 16, 2018  
INVENTOR(S) : Véronique Bodo et al.

Page 1 of 1

It is certified that error appears in the above-identified patent and that said Letters Patent is hereby corrected as shown below:

In the Specification

Column 8,
Line 61, "Blot III;" should read --Blo t III;--.

Column 19,
Line 9, "448/A4        FETUA_HU    FETUA_HU" should read
--448/A4        FETUA_HU    FETUA_HU
                 MAN         MAN--.

Signed and Sealed this
Twentieth Day of August, 2019

Andrei Iancu
*Director of the United States Patent and Trademark Office*

SEQUENCE LISTING

```
<160> NUMBER OF SEQ ID NOS: 19

<210> SEQ ID NO 1
<211> LENGTH: 367
<212> TYPE: PRT
<213> ORGANISM: Homo sapiens

<400> SEQUENCE: 1

Met Lys Ser Leu Val Leu Leu Cys Leu Ala Gln Leu Trp Gly Cys
1               5                   10                  15

His Ser Ala Pro His Gly Pro Gly Leu Ile Tyr Arg Gln Pro Asn Cys
                20                  25                  30

Asp Asp Pro Glu Thr Glu Glu Ala Ala Leu Val Ala Ile Asp Tyr Ile
            35                  40                  45

Asn Gln Asn Leu Pro Trp Gly Tyr Lys His Thr Leu Asn Gln Ile Asp
        50                  55                  60

Glu Val Lys Val Trp Pro Gln Gln Pro Ser Gly Glu Leu Phe Glu Ile
65                  70                  75                  80

Glu Ile Asp Thr Leu Glu Thr Thr Cys His Val Leu Asp Pro Thr Pro
                85                  90                  95

Val Ala Arg Cys Ser Val Arg Gln Leu Lys Glu His Ala Val Glu Gly
                100                 105                 110

Asp Cys Asp Phe Gln Leu Leu Lys Leu Asp Gly Lys Phe Ser Val Val
            115                 120                 125

Tyr Ala Lys Cys Asp Ser Ser Pro Asp Ser Ala Glu Asp Val Arg Lys
        130                 135                 140

Val Cys Gln Asp Cys Pro Leu Leu Ala Pro Leu Asn Asp Thr Arg Val
145                 150                 155                 160

Val His Ala Ala Lys Ala Ala Leu Ala Ala Phe Asn Ala Gln Asn Asn
                165                 170                 175

Gly Ser Asn Phe Gln Leu Glu Glu Ile Ser Arg Ala Gln Leu Val Pro
            180                 185                 190

Leu Pro Pro Ser Thr Tyr Val Glu Phe Thr Val Ser Gly Thr Asp Cys
        195                 200                 205

Val Ala Lys Glu Ala Thr Glu Ala Ala Lys Cys Asn Leu Leu Ala Glu
    210                 215                 220
```

```
Lys Gln Tyr Gly Phe Cys Lys Ala Thr Leu Ser Glu Lys Leu Gly Gly
225                 230                 235                 240

Ala Glu Val Ala Val Thr Cys Thr Val Phe Gln Thr Gln Pro Val Thr
                245                 250                 255

Ser Gln Pro Gln Pro Glu Gly Ala Asn Glu Ala Val Pro Thr Pro Val
            260                 265                 270

Val Asp Pro Asp Ala Pro Pro Ser Pro Pro Leu Gly Ala Pro Gly Leu
        275                 280                 285

Pro Pro Ala Gly Ser Pro Pro Asp Ser His Val Leu Leu Ala Ala Pro
    290                 295                 300

Pro Gly His Gln Leu His Arg Ala His Tyr Asp Leu Arg His Thr Phe
305                 310                 315                 320

Met Gly Val Val Ser Leu Gly Ser Pro Ser Gly Glu Val Ser His Pro
                325                 330                 335

Arg Lys Thr Arg Thr Val Val Gln Pro Ser Val Gly Ala Ala Ala Gly
                340                 345                 350

Pro Val Val Pro Pro Cys Pro Gly Arg Ile Arg His Phe Lys Val
            355                 360                 365
```

<210> SEQ ID NO 2
<211> LENGTH: 345
<212> TYPE: PRT
<213> ORGANISM: Homo sapiens

<400> SEQUENCE: 2

```
Met Ile Ser Pro Val Leu Ile Leu Phe Ser Ser Phe Leu Cys His Val
1               5                   10                  15

Ala Ile Ala Gly Arg Thr Cys Pro Lys Pro Asp Asp Leu Pro Phe Ser
                20                  25                  30

Thr Val Val Pro Leu Lys Thr Phe Tyr Glu Pro Gly Glu Glu Ile Thr
            35                  40                  45

Tyr Ser Cys Lys Pro Gly Tyr Val Ser Arg Gly Gly Met Arg Lys Phe
50                  55                  60

Ile Cys Pro Leu Thr Gly Leu Trp Pro Ile Asn Thr Leu Lys Cys Thr
65                  70                  75                  80

Pro Arg Val Cys Pro Phe Ala Gly Ile Leu Glu Asn Gly Ala Val Arg
                85                  90                  95

Tyr Thr Thr Phe Glu Tyr Pro Asn Thr Ile Ser Phe Ser Cys Asn Thr
            100                 105                 110

Gly Phe Tyr Leu Asn Gly Ala Asp Ser Ala Lys Cys Thr Glu Glu Gly
        115                 120                 125

Lys Trp Ser Pro Glu Leu Pro Val Cys Ala Pro Ile Ile Cys Pro Pro
130                 135                 140

Pro Ser Ile Pro Thr Phe Ala Thr Leu Arg Val Tyr Lys Pro Ser Ala
145                 150                 155                 160

Gly Asn Asn Ser Leu Tyr Arg Asp Thr Ala Val Phe Glu Cys Leu Pro
                165                 170                 175

Gln His Ala Met Phe Gly Asn Asp Thr Ile Thr Cys Thr Thr His Gly
            180                 185                 190

Asn Trp Thr Lys Leu Pro Glu Cys Arg Glu Val Lys Cys Pro Phe Pro
        195                 200                 205

Ser Arg Pro Asp Asn Gly Phe Val Asn Tyr Pro Ala Lys Pro Thr Leu
    210                 215                 220

Tyr Tyr Lys Asp Lys Ala Thr Phe Gly Cys His Asp Gly Tyr Ser Leu
225                 230                 235                 240
```

```
Asp Gly Pro Glu Glu Ile Glu Cys Thr Lys Leu Gly Asn Trp Ser Ala
                245                 250                 255

Met Pro Ser Cys Lys Ala Ser Cys Lys Val Pro Val Lys Lys Ala Thr
            260                 265                 270

Val Val Tyr Gln Gly Glu Arg Val Lys Ile Gln Glu Lys Phe Lys Asn
        275                 280                 285

Gly Met Leu His Gly Asp Lys Val Ser Phe Phe Cys Lys Asn Lys Glu
    290                 295                 300

Lys Lys Cys Ser Tyr Thr Glu Asp Ala Gln Cys Ile Asp Gly Thr Ile
305                 310                 315                 320

Glu Val Pro Lys Cys Phe Lys Glu His Ser Ser Leu Ala Phe Trp Lys
                325                 330                 335

Thr Asp Ala Ser Asp Val Lys Pro Cys
            340                 345

<210> SEQ ID NO 3
<211> LENGTH: 464
<212> TYPE: PRT
<213> ORGANISM: Homo sapiens

<400> SEQUENCE: 3

Met Tyr Ser Asn Val Ile Gly Thr Val Thr Ser Gly Lys Arg Lys Val
1               5                   10                  15

Tyr Leu Leu Ser Leu Leu Leu Ile Gly Phe Trp Asp Cys Val Thr Cys
            20                  25                  30

His Gly Ser Pro Val Asp Ile Cys Thr Ala Lys Pro Arg Asp Ile Pro
        35                  40                  45

Met Asn Pro Met Cys Ile Tyr Arg Ser Pro Glu Lys Lys Ala Thr Glu
    50                  55                  60

Asp Glu Gly Ser Glu Gln Lys Ile Pro Glu Ala Thr Asn Arg Arg Val
65                  70                  75                  80

Trp Glu Leu Ser Lys Ala Asn Ser Arg Phe Ala Thr Thr Phe Tyr Gln
                85                  90                  95

His Leu Ala Asp Ser Lys Asn Asp Asn Asp Asn Ile Phe Leu Ser Pro
            100                 105                 110

Leu Ser Ile Ser Thr Ala Phe Ala Met Thr Lys Leu Gly Ala Cys Asn
        115                 120                 125

Asp Thr Leu Gln Gln Leu Met Glu Val Phe Lys Phe Asp Thr Ile Ser
    130                 135                 140

Glu Lys Thr Ser Asp Gln Ile His Phe Phe Phe Ala Lys Leu Asn Cys
145                 150                 155                 160

Arg Leu Tyr Arg Lys Ala Asn Lys Ser Ser Lys Leu Val Ser Ala Asn
                165                 170                 175

Arg Leu Phe Gly Asp Lys Ser Leu Thr Phe Asn Glu Thr Tyr Gln Asp
            180                 185                 190

Ile Ser Glu Leu Val Tyr Gly Ala Lys Leu Gln Pro Leu Asp Phe Lys
        195                 200                 205

Glu Asn Ala Glu Gln Ser Arg Ala Ala Ile Asn Lys Trp Val Ser Asn
    210                 215                 220

Lys Thr Glu Gly Arg Ile Thr Asp Val Ile Pro Ser Glu Ala Ile Asn
225                 230                 235                 240

Glu Leu Thr Val Leu Val Leu Val Asn Thr Ile Tyr Phe Lys Gly Leu
                245                 250                 255

Trp Lys Ser Lys Phe Ser Pro Glu Asn Thr Arg Lys Glu Leu Phe Tyr
            260                 265                 270
```

```
Lys Ala Asp Gly Glu Ser Cys Ser Ala Ser Met Met Tyr Gln Glu Gly
            275                 280                 285

Lys Phe Arg Tyr Arg Arg Val Ala Glu Gly Thr Gln Val Leu Glu Leu
        290                 295                 300

Pro Phe Lys Gly Asp Asp Ile Thr Met Val Leu Ile Leu Pro Lys Pro
305                 310                 315                 320

Glu Lys Ser Leu Ala Lys Val Glu Lys Glu Leu Thr Pro Glu Val Leu
                325                 330                 335

Gln Glu Trp Leu Asp Glu Leu Glu Glu Met Met Leu Val Val His Met
            340                 345                 350

Pro Arg Phe Arg Ile Glu Asp Gly Phe Ser Leu Lys Glu Gln Leu Gln
        355                 360                 365

Asp Met Gly Leu Val Asp Leu Phe Ser Pro Glu Lys Ser Lys Leu Pro
370                 375                 380

Gly Ile Val Ala Glu Gly Arg Asp Asp Leu Tyr Val Ser Asp Ala Phe
385                 390                 395                 400

His Lys Ala Phe Leu Glu Val Asn Glu Glu Gly Ser Glu Ala Ala Ala
                405                 410                 415

Ser Thr Ala Val Val Ile Ala Gly Arg Ser Leu Asn Pro Asn Arg Val
                420                 425                 430

Thr Phe Lys Ala Asn Arg Pro Phe Leu Val Phe Ile Arg Glu Val Pro
        435                 440                 445

Leu Asn Thr Ile Ile Phe Met Gly Arg Val Ala Asn Pro Cys Val Lys
450                 455                 460

<210> SEQ ID NO 4
<211> LENGTH: 99
<212> TYPE: PRT
<213> ORGANISM: Homo sapiens

<400> SEQUENCE: 4

Met Lys Val Ser Ala Ala Leu Leu Cys Leu Leu Leu Ile Ala Ala Thr
1               5                   10                  15

Phe Ile Pro Gln Gly Leu Ala Gln Pro Asp Ala Ile Asn Ala Pro Val
            20                  25                  30

Thr Cys Cys Tyr Asn Phe Thr Asn Arg Lys Ile Ser Val Gln Arg Leu
        35                  40                  45

Ala Ser Tyr Arg Arg Ile Thr Ser Ser Lys Cys Pro Lys Glu Ala Val
    50                  55                  60

Ile Phe Lys Thr Ile Val Ala Lys Glu Ile Cys Ala Asp Pro Lys Gln
65                  70                  75                  80

Lys Trp Val Gln Asp Ser Met Asp His Leu Asp Lys Gln Thr Gln Thr
                85                  90                  95

Pro Lys Thr

<210> SEQ ID NO 5
<211> LENGTH: 97
<212> TYPE: PRT
<213> ORGANISM: Homo sapiens

<400> SEQUENCE: 5

Met Lys Val Ser Ala Ala Leu Leu Trp Leu Leu Leu Ile Ala Ala Ala
1               5                   10                  15

Phe Ser Pro Gln Gly Leu Ala Gly Pro Ala Ser Val Pro Thr Thr Cys
            20                  25                  30
```

```
Cys Phe Asn Leu Ala Asn Arg Lys Ile Pro Leu Gln Arg Leu Glu Ser
            35                  40                  45

Tyr Arg Arg Ile Thr Ser Gly Lys Cys Pro Gln Lys Ala Val Ile Phe
 50                  55                  60

Lys Thr Lys Leu Ala Lys Asp Ile Cys Ala Asp Pro Lys Lys Lys Trp
 65                  70                  75                  80

Val Gln Asp Ser Met Lys Tyr Leu Asp Gln Lys Ser Pro Thr Pro Lys
                 85                  90                  95

Pro

<210> SEQ ID NO 6
<211> LENGTH: 9
<212> TYPE: PRT
<213> ORGANISM: Homo sapiens

<400> SEQUENCE: 6

Lys Leu Ile Asn Asp Tyr Val Lys Asn
 1               5

<210> SEQ ID NO 7
<211> LENGTH: 12
<212> TYPE: PRT
<213> ORGANISM: Homo sapiens

<400> SEQUENCE: 7

Lys Ala Asp Leu Ser Gly Ile Thr Gly Ala Arg Asn
 1               5                  10

<210> SEQ ID NO 8
<211> LENGTH: 10
<212> TYPE: PRT
<213> ORGANISM: Homo sapiens

<400> SEQUENCE: 8

Lys Glu Gln Leu Ser Leu Leu Asp Arg Phe
 1               5                  10

<210> SEQ ID NO 9
<211> LENGTH: 11
<212> TYPE: PRT
<213> ORGANISM: Homo sapiens

<400> SEQUENCE: 9

Arg Glu Ile Gly Glu Leu Tyr Leu Pro Lys Phe
 1               5                  10

<210> SEQ ID NO 10
<211> LENGTH: 12
<212> TYPE: PRT
<213> ORGANISM: Homo sapiens

<400> SEQUENCE: 10

Arg Asn Leu Ala Val Ser Gln Val Val His Lys Ala
 1               5                  10

<210> SEQ ID NO 11
<211> LENGTH: 16
<212> TYPE: PRT
<213> ORGANISM: Homo sapiens

<400> SEQUENCE: 11

Lys Glu His Ala Val Glu Gly Asp Cys Asp Phe Gln Leu Leu Lys Leu
 1               5                  10                  15
```

```
<210> SEQ ID NO 12
<211> LENGTH: 13
<212> TYPE: PRT
<213> ORGANISM: Homo sapiens

<400> SEQUENCE: 12

Lys Ile Thr Leu Leu Ser Ala Leu Val Glu Thr Arg Thr
1               5                   10

<210> SEQ ID NO 13
<211> LENGTH: 9
<212> TYPE: PRT
<213> ORGANISM: Homo sapiens

<400> SEQUENCE: 13

Lys Phe Ser Val Val Tyr Ala Lys Cys
1               5

<210> SEQ ID NO 14
<211> LENGTH: 19
<212> TYPE: PRT
<213> ORGANISM: Homo sapiens

<400> SEQUENCE: 14

Arg Gln Leu Lys Glu His Ala Val Glu Gly Asp Cys Asp Phe Gln Leu
1               5                   10                  15

Leu Lys Leu

<210> SEQ ID NO 15
<211> LENGTH: 13
<212> TYPE: PRT
<213> ORGANISM: Homo sapiens

<400> SEQUENCE: 15

Lys Leu Asp Gly Lys Phe Ser Val Val Tyr Ala Lys Cys
1               5                   10

<210> SEQ ID NO 16
<211> LENGTH: 22
<212> TYPE: PRT
<213> ORGANISM: Homo sapiens

<400> SEQUENCE: 16

Arg His Thr Phe Met Gly Val Val Ser Leu Gly Ser Pro Ser Gly Glu
1               5                   10                  15

Val Ser His Pro Arg Lys
            20

<210> SEQ ID NO 17
<211> LENGTH: 11
<212> TYPE: PRT
<213> ORGANISM: Homo sapiens

<400> SEQUENCE: 17

Lys Leu Pro Asn Asn Val Leu Gln Glu Lys Ile
1               5                   10

<210> SEQ ID NO 18
<211> LENGTH: 15
<212> TYPE: PRT
<213> ORGANISM: Homo sapiens
```

```
<400> SEQUENCE: 18

Arg Glu Ser Leu Leu Asn His Phe Leu Tyr Glu Val Ala Arg Arg
1               5                   10                  15

<210> SEQ ID NO 19
<211> LENGTH: 16
<212> TYPE: PRT
<213> ORGANISM: Homo sapiens

<400> SEQUENCE: 19

Lys Ala Glu Ser Pro Glu Val Cys Phe Asn Glu Glu Ser Pro Lys Ile
1               5                   10                  15
```